(12) United States Patent  
Naesby

(10) Patent No.: US 6,979,536 B1  
(45) Date of Patent: Dec. 27, 2005

(54) SMALL TRIPLEX FORMING PNA OLIGOS

(75) Inventor: Michael Naesby, Valby (DK)

(73) Assignee: PNA Diagnostics A/S, Glostrup (DK)

( * ) Notice: Subject to any disclaimer, the term of this patent is extended or adjusted under 35 U.S.C. 154(b) by 751 days.

(21) Appl. No.: 09/137,822

(22) Filed: Aug. 21, 1998

(30) Foreign Application Priority Data

Aug. 22, 1997 (EP) .............................. 97114512

(51) Int. Cl.$^7$ ........................ C12Q 1/68; C07H 21/04
(52) U.S. Cl. ..................... 435/6; 435/91.1; 536/23.1
(58) Field of Search .................. 435/6, 91.1; 536/23.1

(56) References Cited

U.S. PATENT DOCUMENTS

| | | | | |
|---|---|---|---|---|
| 5,176,996 A | * | 1/1993 | Hogan et al. ................. | 435/6 |
| 5,422,251 A | * | 6/1995 | Fresco ...................... | 435/91.1 |
| 5,641,625 A | * | 6/1997 | Ecker et al. ................. | 435/6 |
| 5,800,984 A | * | 9/1998 | Vary ......................... | 435/6 |
| 5,834,185 A | * | 11/1998 | Ts'o et al. ................. | 435/6 |
| 5,906,976 A | * | 5/1999 | Vardimon ................... | 514/12 |
| 6,020,126 A | * | 2/2000 | Carlsson et al. ............. | 435/6 |
| 6,027,893 A | * | 2/2000 | Orum et al. ................ | 435/6 |
| 6,403,302 B1 | * | 6/2002 | Dervan et al. ............... | 435/6 |

FOREIGN PATENT DOCUMENTS

WO    WO 92/20702    * 11/1992

OTHER PUBLICATIONS

Corey, David, "Peptide nucleic acids: expanding the scope of nucleic acid recognition", Trends Biotechnology, 15 (6): 224–229, Jun. 1997.*

Svinarchuk, Fedor, "An Unusually Stable Purine(Purine–Pyrimidine) Short Triplex", J. Biol Chem, 270(23): 14068–71, Jun. 9, 1995.*

International Publication No. WO 96/02558 published Feb. 1, 1996.

International Publication No. WO 95/01370 published Jan. 12, 1995.

* cited by examiner

*Primary Examiner*—Jeanine Goldberg  
(74) *Attorney, Agent, or Firm*—Arent Fox PLLC

(57) ABSTRACT

A method for the determination of nucleic acids which is highly specific and simple comprises the formation of a triple stranded binding complex including two separate, different probe molecules and detecting the formation of the complex via the inclusion of one of the probes. The method can be used to differentiate between nucleic acids having a single base difference in sequence.

49 Claims, 5 Drawing Sheets

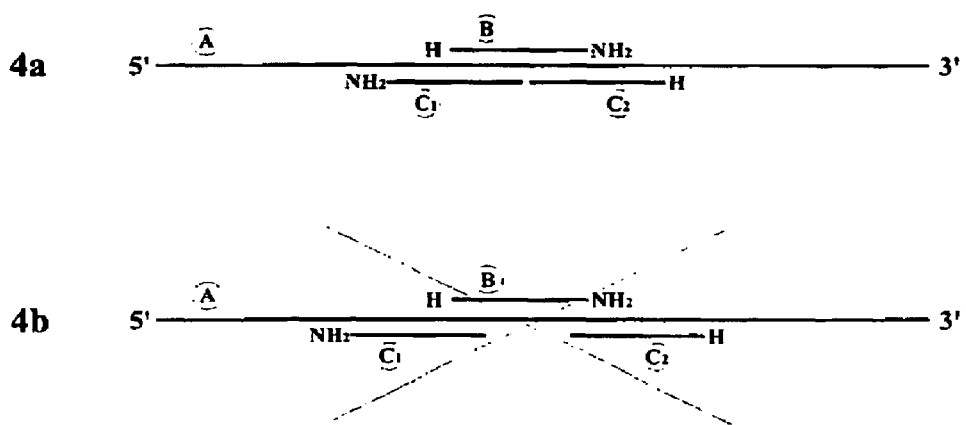
Figure 4
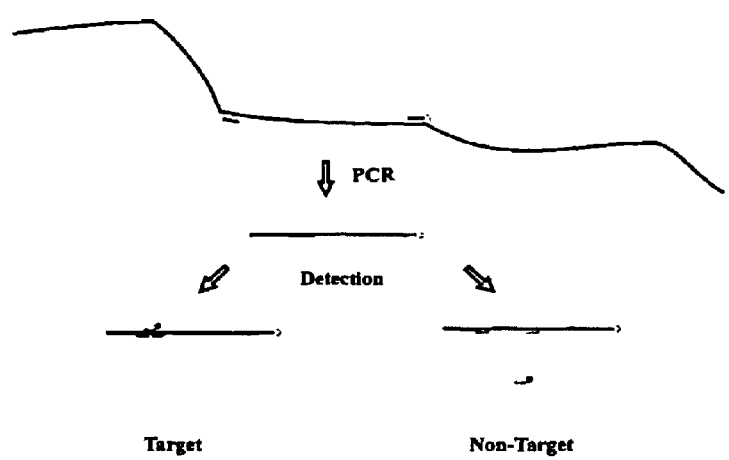
Figure 5
FIG 6a                    FIG 6b
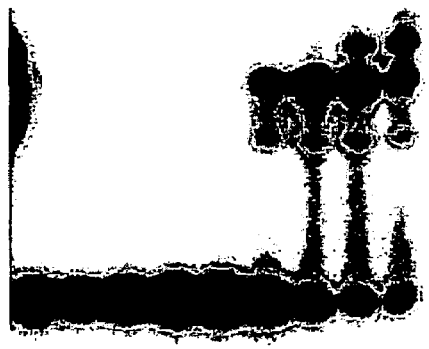
1  2  3  4  5  6  7  8  9          9  8  7  6  5  4  3  2  1

FIG 7a
FIG 7b
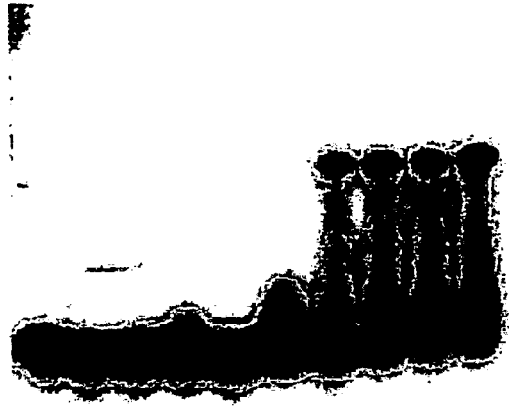
1 2 3 4 5 6 7 8 9 10   1 2 3 4 5 6 7 8 9 10
FIG 8
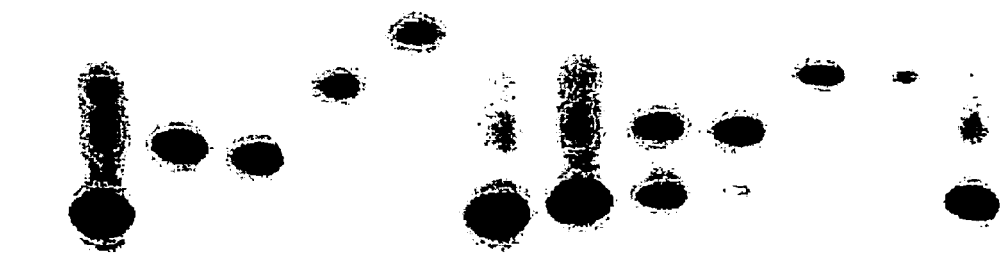
1   2   3   4   5   6   7   8   9   10   11   12
FIG 9

FIG 10
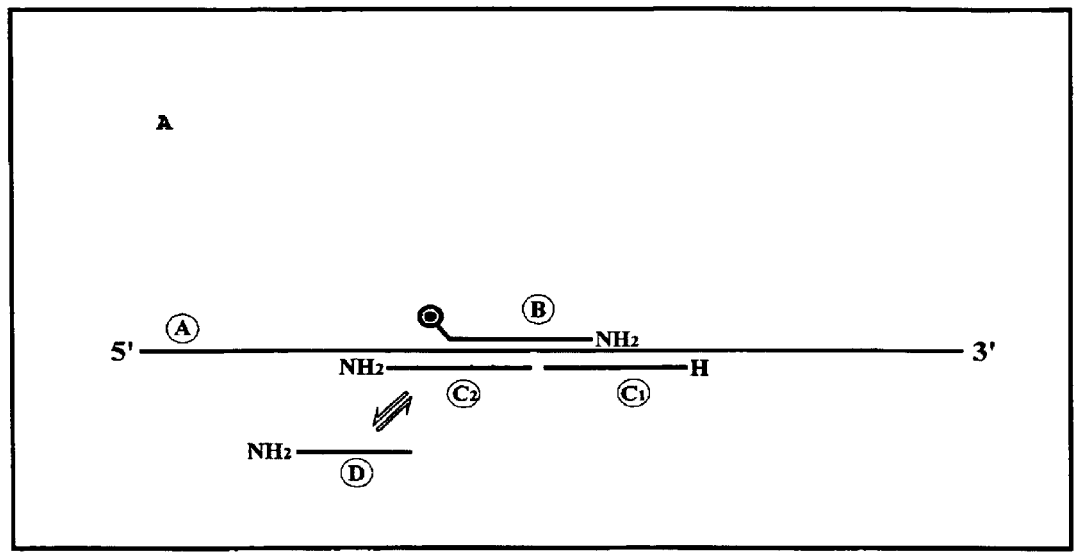
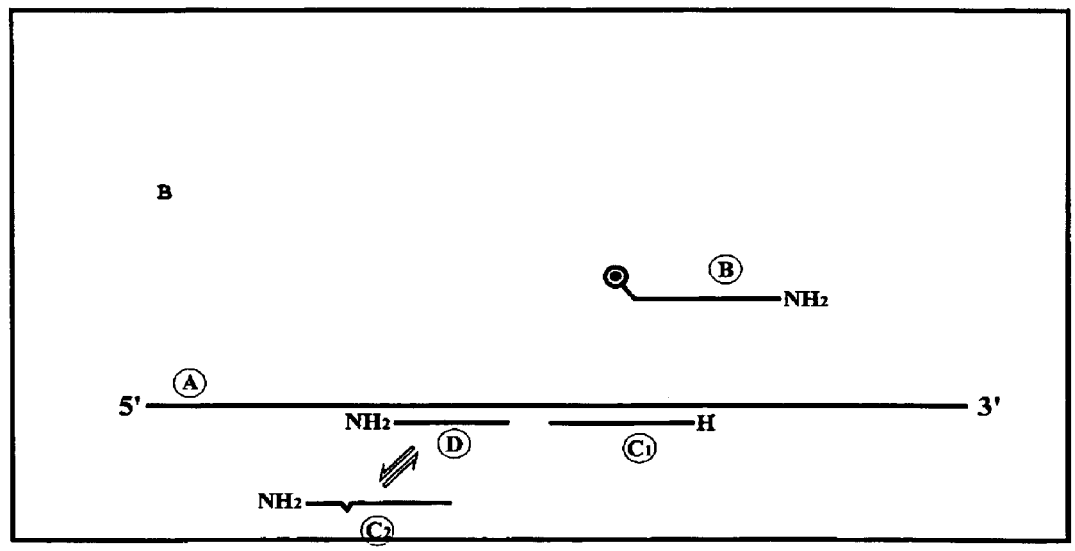

SMALL TRIPLEX FORMING PNA OLIGOS

FIELD OF THE INVENTION

Subject of the present application is a method for the determination of a nucleic acid by forming a triple stranded complex between the nucleic acid to be determined and two or more probe molecules, the thus formed triple stranded binding complex and the use of small triplex forming nucleic acid binding molecules as probes.

BACKGROUND OF THE INVENTION

Detection and quantification of nucleic acid molecules constitutes a fundamental element in several diagnostic techniques. An essential feature of such techniques is the ability of a probe (a nucleic acid or nucleic acid analogue) to hybridize specifically to a complementary nucleic acid sequence. For hybridisation to occur some standard conditions have to be met regarding e.g. salt concentration and temperature, but the major determining factor is the number of fully matched nucleobases in the hybrid of two hybridizing strands. In hybrids of relatively short length, e.g. 6–10 basepairs, a single base pair mismatch will result in a drastic decrease in thermal stability, whereas the relative reduction of stability caused by a single base pair mismatch (or a deletion/insertion) becomes increasingly less with increasing length of the hybrid.

For diagnostic purposes, it is often desirable to identify a sequence of nucleobases which is present only in a particular gene or organism, but absent in any background nucleic acid that may be present in the sample. For a particular sequence of nucleobases to be statistically unique in a typical sample, like e.g. the human genome, the length of the sequence must be in the order of at least 18–20 bases, which on the other hand will enhance its capacity to accomodate mismatches, without dramatic loss of thermal stability.

While recognition of nucleic acids is generally possible by the use of duplex or triplex formation, today primarily duplex forming probes binding single stranded analyte nucleic acid via Watson-Crick (WC) basepairing, are used for diagnostic purposes. Although triplex structures, involving both WC and Hoogsteen binding (H), have been shown to be very thermically stable compared to duplexes, two conflicting properties have seemed to present an obstacle to their exploitation for diagnostic purposes: Because an uninterrupted strand of purine bases is normally required in a triplex forming target sequence, the chance of finding genus or species specific targets within a particular NA sequence is quite small since such a sequence would have to have a certain length in order to be specific. Even if longer, and thus, statistically unique purine sequences were present, the hybridizing properties of any complementary triplex forming probes (high binding capacity per basepair) would cause these to bind unspecifically also to all part sequences down to 6 or 7 bases in length, thus, loosing their specificity.

In WO 92/20702 it is disclosed that certain peptide nucleic acids can strand invade into double stranded DNA and bind DNA with high affinity. In WO 92/20703 the preparation and use of peptide nucleic acids (PNA) as diagnostic probes is disclosed. In WO 95/01370 it is disclosed that two molecules of identical homopyrimidine sequence can form stable triplex structures containing two molecules of the PNA and one molecule of single stranded DNA or RNA. These structures are disclosed for both therapeutic and diagnostic use.

In WO 96/02558 there are disclosed molecules containing two segments of identical sequence, but antiparallel orientation, linked by a bridging moiety. Such molecules are disclosed to exhibit a small but significant increase in Tm compared to the complex formed from independent PNAs each having the sequence of one of the segments. This is ascribed to the high local concentration of the covalently linked PNA strands. The segments disclosed are generally 6 or more bases in length. The linked peptide nucleic acids of this disclosure suffer from the priniciple problem that for sufficient sequence specificity of binding there is a need for a relatively large pyrimidine stretch, corresponding to a complementary purine stretch in the analyte nucleic acid, which would lead to very high levels of unspecific binding.

It is an object of the present invention to provide sequence specific complexes containing three independent strands bound by triple helix formation, wherein one of the strands is a short triplex forming probe molecule.

SUMMARY OF THE INVENTION

Subject of the present invention is a method for the determination of a nucleic acid A comprising-forming a triple stranded binding complex between said nucleic acid A, a first nucleic acid A binding molecule B and at least one further nucleic acid A binding molecule C having a base sequence different from the sequence of B and determining the presence or amount of said binding complex as a measure for the presence or amount of said nucleic acid, wherein the triple stranded complex is formed under conditions for which the triple stranded complex between A, B and the one or more different molecules C is more thermostable than a triple stranded complex formed by two molecules of B or two identical molecules of C, with one molecule of A.

A further subject of the invention is the finding that the goal can be achieved by stabilizing a short Hoogsteen (H) binding oligomer by a longer Watson-Crick (WC) binding oligomer. This bypasses the requirement for a long homopurine tract in a specific target sequence and, at the same time, makes it possible to exploit the high discriminative power of short Hoogsteen binding probes without loss of specificity.

A further subject of the invention is a triple stranded binding complex between a nucleic acid A, a first nucleic acid binding molecule B and at least one further nucleic acid binding molecule C having a different base sequence than B, characterized in that it is more thermostable than a triple stranded complex formed from two molecules B or two identical molecules of C, with one molecule A.

A further subject of the invention is the use of a nucleic acid binding molecule having a length of from 4 to 10, preferably from 5 to 8, bases as a probe for specifically determining a nucleic acid.

A further subject of the invention is the controlled binding of a short triplex-forming oligomer (B) under conditions where it will not, by itself, form stable hybrids with a nucleic acid (A), through the controlled binding of one or more, duplex forming, mixed sequence oligomer(s) (C).

Further subjects of the invention are disclosed in the subclaims.

BRIEF DESCRIPTION OF THE DRAWINGS

FIG. 4 shows that in an arrangement of FIG. 3 the two probes C1 and C2 must be bound adjacently within the triple helical binding region for stable triplex formation to occur.

FIG. 5 shows a preferred embodiment of the present invention, wherein the nucleic acid is labelled during amplification and the correct amplicons are determined by the use of a differently labelled probe B.

FIGS. 6a, 6b, 7a, 7b and 8 show the results of experiments performed in the examples 1 to 3.

FIG. 9 shows a first mode to destabilize $AB_2$.

FIG. 10A shows the case where the nucleic acid to be determined (A) fully matches both probe C2 and probe D but probe C2 has the higher affinity for the nucleic acid to be determined. In this case the triple helical structure can be formed, because C1 and C2 after binding are only separated by a nick. In FIG. 10B the case is shown where the target nucleic acid (A) has a mismatch with respect to C2, but not with competitor probe D. This situation favours binding of D to the target resulting in a gap between D and C1 which will prevent formation of the triple helix. Thus, the nucleic acid not to be determined can be discriminated from the nucleic acid to be determined.

DETAILED DESCRIPTION OF THE INVENTION

Figure 1:
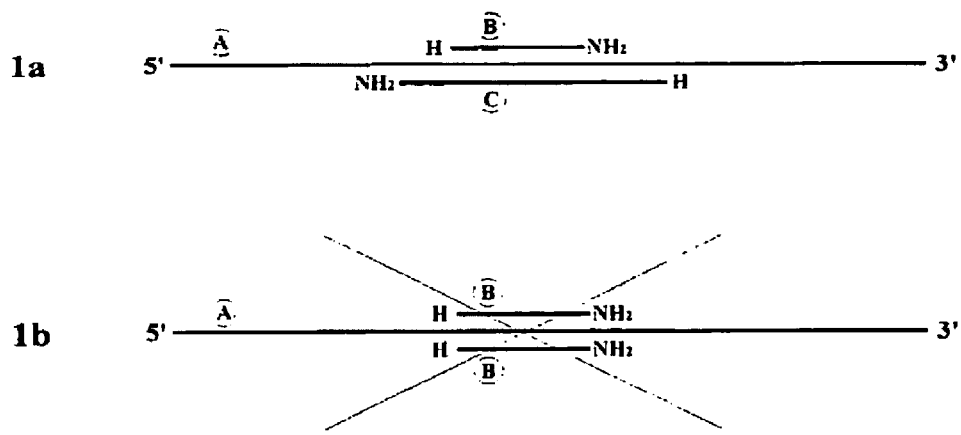
FIG. 1a and FIG. 1b shows the theoretically possible triple stranded complexes formed in a mixture containing the analyte nucleic acid A, a shorter probe B and a longer probe C. With appropriate conditions of hybridization, formation of the complex 1a is favoured over the formation of complex 1b for a specific analyte nucleic acid A.

The nucleic acid A to be determined is understood in the present invention as an analyte nucleic acid or a nucleic acid derived therefrom. Analyte nucleic acids include nucleic acids of any origin, for example, nucleic acids of plant, animal, human, viral, bacterial, or non-natural origin. They may be present in solution, suspension, but also fixed to solid supports or contained in cell-containing media, cell smears, fixed cells, tissues, or fixed organisms. Nucleic acids derived therefrom are nucleic acids prepared from analyte nucleic acids or parts thereof, for example as copies of the above-mentioned nucleic acids, or parts thereof. These copies include nucleic acids generated from that original analyte nucleic acid by amplification, including any replication or/and transcription/reverse transcription reactions, for example the polymerase chain reaction.

Samples containing the nucleic acid to be determined are often pre-treated to make the analyte accessible for hybridization. Such pretreatment may include cell lysis and denaturing of double-stranded nucleic acids by changing the pH into the alkaline region, repeating extreme temperature changes (freezing/thawing), changing the physiological probe conditions (osmotic pressure), use of detergents, chaotropic salts or enzymes (e.g. proteases, lipase). These steps may be used either alone or in combination in order to release the nucleic acids in an accessible form. In some instances, it may be advantageous to separate the nucleic acids from other components of the sample, like proteins, cells, cell fragments, but also nucleic acids which are not intended to be detected. In addition, it may be advantageous to denature the analyte nucleic acid to make it single stranded and free of secondary structures.

A nucleic acid binding molecule according to the present invention is a molecule recognizing a sequence of nucleobases on nucleic acid A through hydrogen bonding as generally known from the natural recognition of nucleobases in double-stranded nucleic acids, like between the bases A and T or U and between the bases C and O. The recognition can for example occur between naturally occurring nucleobases, but also between natural bases and non-natural bases and between non-natural bases and non-natural bases. Non-natural bases are for example bases as outlined in WO 96/02558, especially iso-pyrimidine heterocyclic bases. Those hydrogen bonding moieties are attached to a backbone in a consecutive way, such that binding can occur. Suitable backbones are the naturally occurring phosphate sugar backbone (like in nucleic acids, DNA and RNA) and any non-naturally occurring backbones (like in peptide nucleic acids (PNA)).

Preferably the nucleic acid binding molecules have a polymeric backbone different from the natural sugar phosphate backbone. Examples of such probe molecules are now well-known in the art. Those probes may be based upon monomeric subunits, which are linked in a repetitive way. It is preferable that the probe molecule contains monomeric subunits being connected to other monomeric subunits by peptide bonds. The peptide bond is understood to be the bond connecting a primary or secondary amine and a carboxylic acid residue. Other types of linkages within the monomers or connecting one or more monomers in the backbone are possible, for example, ether or amino bonds. Examples of such probe molecules are described in WO 92/20702 including probe molecules having ligands bound to aza-nitrogen atoms, WO 94/25477, and WO 96/20212. Probe molecules having mixed different linkages between the monomers are described in EP-A-0 672 677.

The term probe molecule further contains molecules having the above stretch of the non-natural backbone and an additional stretch of the natural sugar phosphate backbone. Such chimera may possess somewhat lower affinity to complementary nucleic acids, but are nevertheless usable in the present invention.

The term backbone in the present invention shall mean the polymeric moiety to which at different points of attachment heterocyclic base moieties are bound in a consecutive way, wherein the distances between the atoms used for the attachment of a base moiety on the backbone are separated from each other by a stretch of from 4 to 8, preferably 6 atoms, most preferably including the peptide group (CONH).

Preferred probe molecules are compounds of the general formula I

Formula I

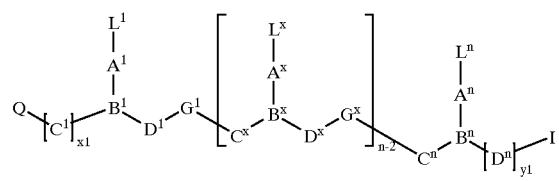

wherein n is an integer of from at least 3, x is an integer of from 2 to n−1, each of $L^1$–$L^n$ is a ligand independently selected from the group consisting of hydrogen, hydroxy, ($C_1$–$C_4$)alkanoyl, naturally occurring nucleobases, non-naturally occurring nucleobases, aromatic moieties, DNA intercalators, nucleobase-binding groups, heterocyclic moieties, reporter ligands and chelating moieties, wherein at least one of $L^1$–$L^n$, preferably at least one of $L^2$–$L^n$ is a non-nucleobase electron acceptor or a donor moiety and at least 2 of $L^1$–$L^n$ being a nucleobase binding group, or a naturally or non-naturally occurring nucleobase, each of $C^1$–$C^n$ is $(CR^6R^7)_y$ (preferably $CR^6R^7$, $CHR^6CHR^7$ or $CR^6R^7CH_2$) where $R^6$ is hydrogen and $R^7$ is selected from the group consisting of the side chains of naturally occurring alpha amino acids, or $R^6$ and $R^7$ are independently selected from the group consisting of hydrogen, $(C_1$–$C_6)$alkyl, aryl, aralkyl, heteroaryl, hydroxy, $(C_1$–$C_6)$ alkoxy, $(C_1$–$C_6)$alkylthio, $NR^3R^4$ and $SR^5$, where $R^3$ and $R^4$ are as defined below, and $R^5$ is hydrogen, $(C_1$–$C_6)$ alkyl, hydroxy, $(C_1$–$C_6)$alkoxy, or $(C_1$–$C_6)$alkylthio-substituted $(C_1$–$C_6)$alkyl or $R^6$ and $R^7$ taken together complete an alicyclic or heterocyclic system; or $C^1$–$C^n$ is CO, CS, $CNR^3$;

each of $D^1$–$D^n$ is $(CR^6R^7)_z$ (preferably $CR^6R^7$, $CHR^6CHR^7$ or $CH_2CR^6R^7$) where $R^6$ and $R^7$ are as defined above, each of y and z is zero or an integer from 1 to 10, the sum y+z being at least 2, preferably greater than 2, but not more than 10, each of $G^1$–$G^{n-1}$ is $—NR^3CO—$, $—NR^3CS—$, $—NR^3SO—$ or $—NR^3SO^{2-}$, in either orientation, where $R^3$ is as defined below;

each of $A^1$–$A^n$ and $B^1$–$B^n$ are selected such that:
(a) $A^1$–$A^n$ is a group of formula (II/A), (II/B). (II/C) or (II/D), and $B^1$–$B^n$ is N or $R^3N+$ or
(b) $A^1$–$A^n$ is a group of formula (II/D) and $B^1$–$B^n$ is CH;

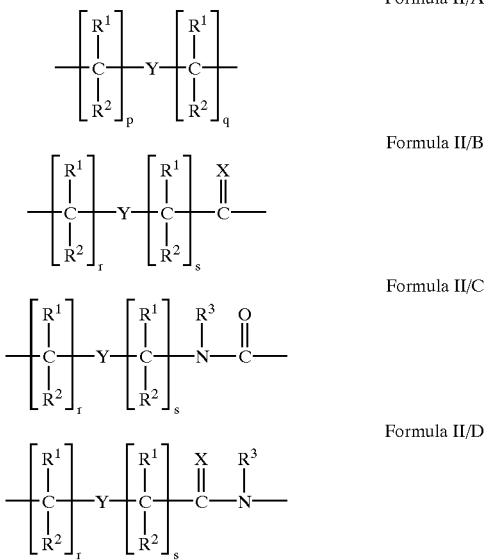

Formula II/A

Formula II/B

Formula II/C

Formula II/D wherein:
X is O, S, Se, $NR^3$, $CH_2$ or $C(CH_3)_2$;
Y is a single bond, O, S or $NR^4$,
each of p and q is zero or an integer from 1 to 5, (the sum p+q being preferably not more than 5),
each of r and s is zero or an, integer from 1 to 5, (the sum r+s being preferably not more than 5),
each $R^1$ and $R^2$ is independently selected from the group consisting of hydrogen, $(C_1$–$C_4)$alkyl which may be hydroxy- or $(C_1$–$C_4)$alkoxy- or $(C_1$–$C_4)$alkylthio-substituted, hydroxy, $(C_1$–$C_4)$alkoxy, $(C_1$–$C_4)$alkylthio, amino and halogen, each $R^3$ and $R^4$ is independently selected from the group consisting of hydrogen, $(C_1$–$C_4)$alkyl, hydroxy- or alkoxy- or alkylthio-substituted $(C_1$–$C_4)$alkyl, hydroxy, $(C_1$–$C_6)$-alkoxy, $(C_1$–$C_6)$-alkylthio and amino, Q and I is independently selected from $—CO_2H$, $—CONR'R''$, $—SO_3H$ or $—SO_2NR'R''$ or an activated derivative of $—CO_2H$ or $—SO_3H$ and $—NR'R'''$ where R', R" and R'" are independently selected from the group consisting of hydrogen, alkyl, amino protecting groups, reporter ligands, intercalators, chelators, peptides, proteins, carbohydrates, lipids, steroids, nucleosides, nucleotides, nucleotide diphosphates, nucleotide triphosphates, oligonucleotides, including both oligoribonucleotides and oligodeoxyribo-nucleotides, oligonucleosides and soluble and non-soluble polymers and as well as nucleic acid binding moieties and each of x1 and y1 is an integer of from 0 to 10.

Preferred probes contain at least one monomer subunit of the formula III

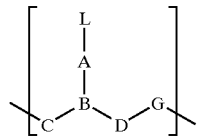

Formula III wherein for A, B, C, D. G, L the above definitions for $A^x$, $B^x$, $C^x$, $D^x$, $G^x$, and $L^x$ apply.

Alkoxy- and alkylthio groups contain preferably from 1 to 4 carbon atoms.

An example for a fused aromatic moiety is naphthol. A heterocyclic moiety is for example pyridin. Reporter groups are moieties that can be detected, like fluorescent compounds, for example fluorescein, or moieties that can be recognized by another molecular entity, like haptens which can be recognized by an antibody raised against this hapten.

In the above structures wherein Q or I is an oligonucleotide or oligonucleoside, such structures can be considered chimeric structures between PNA compounds and the oligonucleotide or oligonucleoside.

Linkers $A^1$–$A^n$ for binding acceptor moieties are generally preferred at a length of between 1 to 10 atoms, most preferred 2 to 6 atoms, for donor moieties at a length of 1 to 10, most preferred 2 to 8 atoms.

More preferable are compounds of subgroups Ia–Ib based on the general formula I wherein (Ia): $B^1$–$B^n$ is N and $A^1$–$A^n$ is $—CO—(CH_2)_6—$
(Ib): $B^1$–$B^n$ is N and $A^1$–$A^n$ is $—CO—NR^3—(CH_2)_2—$
(Ic): $B^1$–$B^n$ is CH and $A^1$–$A^n$ is $—NR^3—CO—(CH_2)_2—$ Preferred PNA-containing compounds useful to effect binding to RNA, ssDNA and dsDNA and to form triplexing structures are compounds of the formula IVa, IVb and IVc:

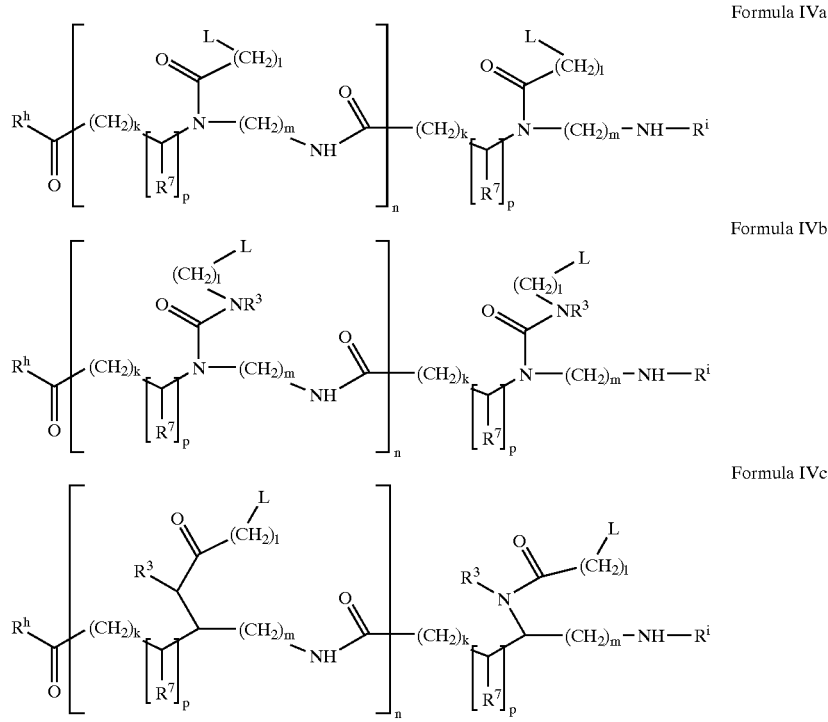

Formula IVa

Formula IVb

Formula IVc wherein:
each L is independently selected from the definitions of $L^1$–$L^n$ in formula I,
each $R^7$ is independently selected from the group consisting of hydrogen and the side chains of naturally occurring alpha amino acid,
n is an integer greater than 1,
each k, l, and m is, independently, zero or an integer from 1 to 5,
each p is zero or 1, and
$R^h$ and $R^i$ are as defined for R', R" and R'".

Labels are generally known as moieties that are themselves immobilizable or detectable or can be immobilized/detected by coupling to additional moieties. Examples of labels are fluorescent moieties, (e.g. fluoresceine or rhodamine), enzymes, (e.g. peroxidase or phosphatase), immunologically active substances, like haptens, (e.g. digoxigenin), or protein binding tags (e.g. biotin) etc.

Most preferred nucleic acid binding compounds comprise at least one monomeric subunit of the general formula V:

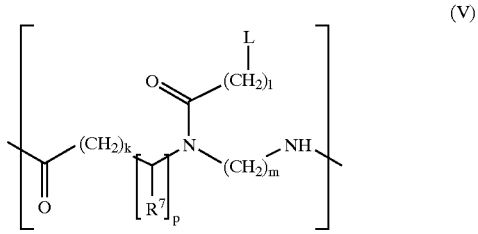

(V)

wherein
L is a ligand as defined above for $L^1$–$L^{n'}$
k, l and m is independently zero or an integer from 1 to 5,
p is zero or 1, and
$R^7$ is selected from the group consisting of hydrogen and the side chains of naturally occurring alpha amino acids.

These compounds can be prepared analogous to the synthesis described in WO 92/20702, WO 94/25477, WO 96120212, EP-0 672 677 and EP-0 700 928. A preferred way to produce the compounds of general formula I is the step-wise chemical synthesis according to WO 92/20702; incorporating as a monomer a compound of the general formula VIa–VIc

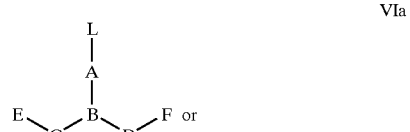

VIa

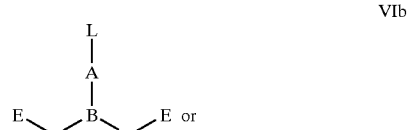

VIb

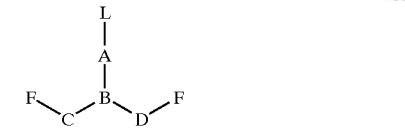

VIc wherein the definitions of A, B, C and D are chosen from the definitions of $A^1$–$A^n$, $B^1$–$B^n$, $C^1$–$C^n$ and $D_1$–$D^n$ formula I, respectively with the condition that any amino groups therein may be protected by amino protecting groups; E is COOH, CSOH, SOOH, $SO_2OH$ or an activated derivative thereof; F is $NHR^3$ or $NPgaR^3$, where $R^3$ is as defined above and Pga is an amino protecting group and L is defined as above or a protected derivative thereof.

Preferred monomers are amino acids having formula (VI)

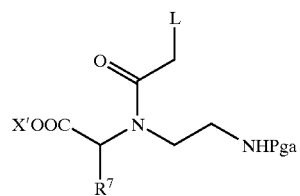

VII wherein X is a carboxylic acid protection group or hydrogen, $R^7$ is independently selected from the group consisting of hydrogen and the side chains of naturally occurring alpha amino acids, or amino-protected and/or acid terminal activated derivatives thereof.

The sequences of B and C are preferably choosen such that at least one of them is selective for the analyte nucleic acid. Preferably B is unselective and C is selective, inferring that the sequence bound by B is shorter than the sequence bound by C.

Further the complex ABC is preferably more stable than the double helix of A and its complement A (as for example in natural dsDNA), if such complement is present in the sample.

The molecular structure of nucleic acid binding molecules B and C (apart from the sequence requirements) can generally be either the same or different. However, it is much preferred that at least one of molecules B and C is a nucleic acid binding compound comprising a non-naturally occurring backbone. Most preferred both of molecules B and C are nucleic acid binding compounds with a non-natural backbone. In the following molecules B and C are referred to as probes. The general requirement for the formation of a complex according to the present invention is that molecules A, B and C are capable of forming a triple helical structure within a region which is in the following termed the triple stranded region. It is therefore preferred according to the invention, that the probes, binding within this region, do not contain any sugar phosphate backbone units.

A core of the present invention is the formation of a complex containing at least the nucleic acid strand A, one binding molecule B, and at least one further nucleic acid binding molecule C having a base sequence different from the sequence of B. These at least three molecules are incubated under conditions such that a triple stranded complex is formed containing all of these molecules. Any other complexes containing the nucleic acid A and molecule B should not be formed to a detectable or interfering extent. This can be achieved in several ways, some of which being related to the construction of molecule C.

In a first embodiment, the triple stranded complex contains the nucleic acid A, one molecule of B and one molecule of C in the triple stranded region. In a preferred embodiment, the triple stranded region of ABC has a length of more than 3, but less than 11, preferably more than 4, but less than 9, bases. Molecule B should therefore have a length covering this region. However, molecule B can have attached other moieties, which do not conflict with its capability to participate in the triple stranded structure. Such moieties can include labels, or further recognizing moieties, like nucleic acid binding molecules which do not participate in the triple stranded structure, for example used as specifically recognizable sequences for binding a secondary probe. Preferably the part of B participating in the triple helix formation does not contain any non-pyrimidine bases.

In practical manner, molecule C contains a region Cy participating in the triple strand formation by binding in a WC mode to the nucleic acid A. In addition, molecule C has, at one or both ends of segment Cy, one or more further segments binding nucleic acid A, preferably by double helix formation with nucleic acid A. Most preferably these segments have a length of from 1 to 20, more preferable from 2 to 8 and most preferable from 2 to 4 bases. Those segments will be termed Cx and Cz in the following. In the case that C has a segment Cx and a segment Cz, those segments can be of either equal or different length. The binding region of molecule C in this embodiment therefore includes a triplex forming region and one or two duplex forming regions. The length of molecule C should be choosen as generally acknowledged by a man skilled in the art. This means that the length of molecule C should be such that it is selective. This of course depends upon the occurrence of nucleic acids in the sample and their similarity in sequence to the nucleic acid A. In special cases the length of C need not be more than 6–9 bases, but generally, for sufficient discrimination of similar sequences, the binding sequence of C should be in the range of from 10 through 40 basepairing units. The preferred overall nucleic acid A binding length of molecule C is at least 12 bases, because molecule C in the preferred embodiment of the present invention is used to contain the base information to distinguish between nucleic acid A and nucleic acids not to be determined.

This embodiment of the invention is exemplified in FIG. 1. Depending on the conditions of hybridization a short PNA oligo (B) will bind to the analyte (A) via Hoogsteen basepairing only when stabilized by another, longer PNA oligo (C) binding to the analyte (A) by Watson-Crick basepairing (see 1a). Under similar conditions of hybridization two molecules of the short PNA oligo (B) are not able to form stable triplex structures with the analyte (A) (see 1b), and neither does B alone form a stable duplex with A.

The selectivity of C for A can be located within any segment of C. However, according to the present invention, and in view of the fact that only very few nucleic acids can be discriminated on the basis of short purine stretches, molecule C may be designed to be specific to the nucleic acid sequence to be determined in at least one of the segments Cx and Cz. In order to achieve selectivity, these segments extend from the purine stretch for binding molecule B such that the segment Cx or Cz embraces the sequence difference between nucleic acid A and the nucleic acid not to be determined (thus creating a mismatch to the nucleic acid not to be determined).

Figure 2:
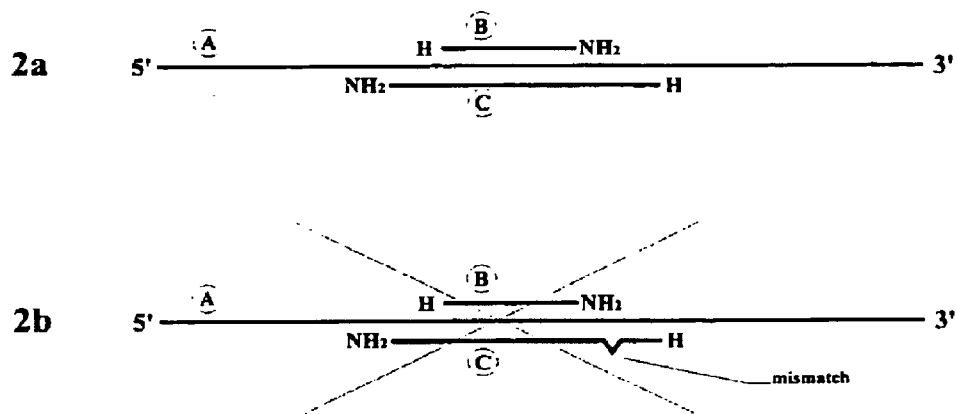
In FIG. 2a and FIG. 2b it is shown that a complex 2b including a probe C having a mismatch outside the triple helical binding region disfavours the formation of a complex compared to the complex 2a including the fully matched probe C.

This embodiment is exemplified in FIG. 2. A triplex structure formed between the analyte (A), a short Hoogsteen binding PNA oligo (B) and a Watson-Crick binding PNA oligo (see 2a) will be destabilized if a mismatch is introduced, also outside the triplex region delimited by (B), and the triplex structure (see 2b) will not be formed.

In a second embodiment, mismatches between molecule C and any nucleic acids not to be determined may be located within the other segments, including segment Cy. This will in addition destabilize the formation of the triple stranded complex of C with the nucleic acid not to be determined and the molecule B.

In a second major form of the invention the triple stranded region contains an additional molecule C, such that the triple stranded complex will contain the analyte nucleic acid A, a molecule B and two separate molecules C (in the following termed C1 and C2). Each of these molecules C may have a length of from 5 to 40 bases. In order to create this complex, the molecules C each comprises a segment Cy (Cy 1 and Cy2 respectively) which are together capable of forming a triple stranded structure with the binding region of the analyte nucleic acid (A) and one molecule B. The sequence of each of the segments (Cy) is chosen such that exclusive binding to the analyte nucleic acid is performed. Exclusive in this connection means that the binding region of segments Cy 1 and Cy2 on A do not overlap. Preferably these binding regions are adjacent to each other, such that when bound, C1 and C2 form a very small gap, preferably of from 2 to 1 nucleotides, most preferable a nick (no nucleotide) between the ends of segments Cy 1 and Cy2. C1 and C2 can independently contain segments Cx or Cz designed for double-stranded binding of probes C1 and C2 to the analyte nucleic acid. These segments Cx and Cz are preferably bound to segments Cy1 and Cy2 at ends of these segments pointing away from each other. C1 and C2 preferably do not contain any segments at the ends of Cy 1 and Cy2 pointing towards each other.

Figure 3:
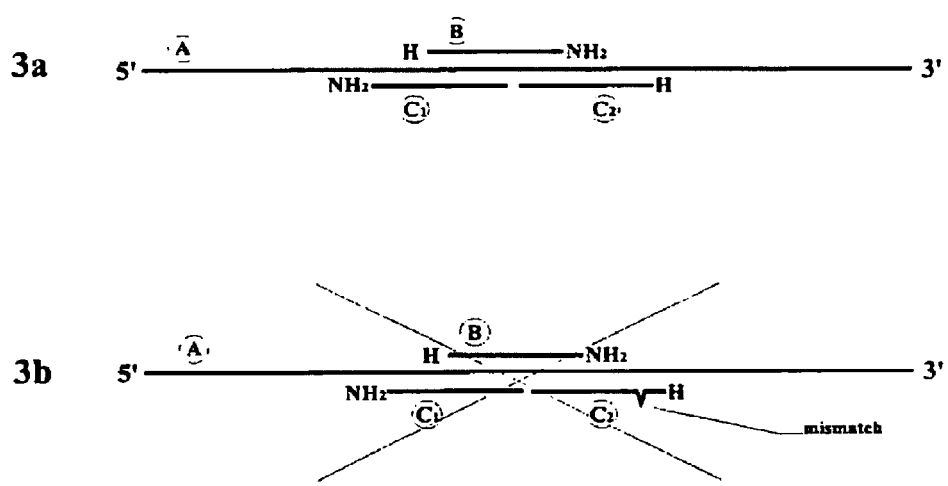
FIG. 3 shows the same arrangement as FIG. 2, however, characterized in that instead of a single longer probe C there are used two smaller probes C1 and C2.

A drawing showing this embodiment is contained in FIG. 3. Depending on the conditions of hybridization a short PNA oligo (B) can bind to the analyte (A) via Hoogsteen basepairing when stabilized by two adjacently bound PNA oligos (C 1 and C2) binding to the analyte (A) by Watson-Crick basepairing (see 3a). If a mismatch is introduced in C 1 or C2, also outside the triplex region delimited by B, the whole triplex structure (see 3b) will be destabilized and will not be formed. In the embodiment using two molecules C1 and C2, the specificity of the method is substantially enhanced. Due to the fact that formation of the complete triple stranded complex is a distinguishing factor between analyte and non-analyte nucleic acids, the present invention is also highly suitable for the determination of analyte nucleic acids differing from nucleic acids not to be determined by deletions or insertions. Such an arrangement is shown in FIG. 4. When two PNA oligos (C1 and C2), hybridizing by Watson-Crick basepairing, are bound adjacently to each other on the analyte (A), they can act together to promote the binding of a short PNA oligo (B), hybridizing via Hoogsteen basepairing to (A), and a triplex structure will be formed (see 4a). If one or more bases are introduced in (A) between the target sites of the two Watson-Crick binding PNA oligos (see 4b) they will not be able to stabilize the short PNA oligo (B) which will, thus, not bind to the analyte (A).

In embodiments wherein two independent probes C1 and C2 are used, there is no strict requirement that the triple strand binding region of B is smaller than molecules C. Instead of this, the requirement is that the triple strand binding region of B is smaller than the overall length of the binding region of molecules C1 and C2. The triple stranded binding regions of each of the molecules C1 and C2 are generally smaller than the triple strand binding region of B.

In a further embodiment which is very useful in discriminating between nucleic acids of very similar base sequence, for example between alleles, bacterial species, subspecies, or even specific strains in addition to the probes B and C a further probe D is used. Probe D will be a competitor probe which is capable of binding to nucleic acid A instead of one of the probes C, and which will differ from said probe C in length, and/or binding position, and/or sequence, and/or modifications of nucleobases.

In a preferred embodiment, which is schematically shown in FIG. 10a reaction mixture is provided containing the target nucleic acid A, probe molecule B, two probe molecules C1 and C2, as well as a competitor probe molecule D. Preferably in this case the competitor probe is the discriminative probe (i.e. the difference in sequence of the nucleic acid to be determined and the nucleic acid not to be determined is found in the binding region of probe D). The competitor probe has a sequence fully complementary to a part of the target A, but lacks one or more distal nucleotides resulting in a gap between D and C1. If probe C2 has a sequence fully complementary to the nucleic acid to be determined (A), then C2, rather than the competitor (D), will hybridize to A and allow triplex formation. If probe C2 has a mismatch with respect to the target A, then the competitor (given the appropriate composition and concentration) will hybridize to A instead of C2 and a gap will be formed which will not allow triplex formation.

In the case of specific determination of a target A, corresponding to sequences from Mycobacterium interjectum, a competitor molecule D, complementary to part of this target sequence, is added to the sample together with probes B and C 1 and C2. When using a molecule C2 fully complementary to M. interjectum and with higher affinity than D, this molecule (together with C1) would allow triplex formation including B. When using other C2 molecules, not fully matched, these molecules would be outcompeted by the competitor D, and a gap would be formed not allowing triplex formation. This way spurious triplex formation as a consequence of crosshybridization of mismatched C2 probes were prevented. Thus, the use of such competitor probes provides a much better possibility to discriminate between closely related nucleic acids.

A triple strand binding region in any of the nucleic acids or nucleic acid binding molecules mentioned is defined to be a region of this nucleic acid or molecule either basepairing with two other strands of nucleic acids or molecules or basepairing with bases which are themselves basepairing with two strands of nucleic acids or molecules. A double helix forming region is defined to be a region or sequence of a molecule basepairing with bases of only one strand of another nucleic acid or molecule (e.g. segments Cx and Cz, binding adjacently to the triple stranded region on the analyte nucleic acid A). In this case preferably Watson-Crick basepairing occurs, while in triple strand binding both Watson-Crick basepairing and Hoogsteen basepairing occur. This double helix forming region may be as small as 1 basepair, but may be as long as 100 basepairs.

It is a core of the present invention that molecules B and C are not linked together. This is important in order that one of the molecules will not force the other of the molecules into the triple helical complex by locally increasing the concentration of this other molecule artificially. A background of the present invention is the fact that the mere binding of one or two molecules C enables the binding of a molecule B in a triple helical mode. The formation of the triple stranded complex between A, B and C, however, will only occur if it is more thermostable than a triple stranded complex formed by two molecules of B, or by two identical molecules of C, with one molecule of A.

There are at least three preferred ways to achieve higher thermostability of the correct triple stranded complex (formed from A, B and C, now termed ABC). The inclusion of molecule C in favour of a second molecule of B into the triple stranded region can be readily achieved due to the fact that the nucleic acid A binding region of molecule C is longer than the nucleic acid A binding region of B. Thus, the length of C (and in some situations also of B) can be varied to obtain optimal ABC triplex formation.

In another embodiment molecule B and/or C has been chemically modified in at least one position, destabilizing triple helix formation of two molecules B with one molecule A (see FIG. 9) and of two identical molecules C with one molecule A. Such modifications are for example chemical groups, for example charged groups, like carboxy- or aminogroups, or organic chemical groups, like acyl groups, or benzoyl groups, bound to any atom of molecules B and/or C. A preferred arrangement of these groups is when the sequence of the probes is chosen such that, when bound to the analyte nucleic acid, the chemical groups of two identical molecules (B or C) are brought into close proximity, causing destabilization of the overall triple helical complex The size and nature of such chemical groups can be used to fine tune binding characteristics, and should be chosen in a way that the formation of the correct triple stranded complex (including A, B and C) is not affected. In a third way of the invention the triple binding region has an asymmetric base sequence, such that in the preferred binding mode, the triple stranded binding region in $AB_2$ and $AC_2$ would be very small. The preferred binding mode in triple stranded complexes of course depends upon the chemical structure of the molecules chosen. For example for peptide nucleic acids the preferred triple stranded binding mode is antiparallel to each other, meaning that amino ends of the two molecules are facing in opposite directions, one pointing to the 3'-end of the analyte nucleic acid and the other pointing to the 5'-end of the analyte nucleic acid. Therefore, it is preferred to choose an asymetric binding region (an asymetric base sequence) of the analyte nucleic acid A, and to synthesize C and B with opposite directions so that they will bind in an antiparallel mode with respect to each other.

Regarding peptide nucleic acid oligos, triplex formation with nucleic acid is also possible for two molecules pointing in the same direction. Although these complexes are less stable than when two PNA molecules are bound in opposite directions there is a possibility that two molecules of B or two identical molecules of C will form triplex with the analyte nucleic acid A, and thus interfere with formation of the correct complex ABC. Destabilization of both $AB_2$ and $AC_2$ has been described above. In addition the formation of $AC_2$ can be prevented by performing the binding reaction under alkaline conditions, while including modified bases like e.g. pseudoisocytosine in molecule B but not in C. Under alkaline conditions cytosine is not protonated, and can not participate in Hoogsteen binding, whereas pseudoisocytosine is independent of the pH of the reaction solution. Pseudoisocytosine and other modified bases are described in WO 96/02558.

The sample containing the nucleic acid to be determined (A) is supplied with the probe molecules B and C in order to create the complex ABC between these probe molecules and the nucleic acid to be determined. This complex will form via base-mediated hydrogen bonding. The binding of the probe molecules to the nucleic acid will happen according to conditions, known to one skilled in the art, for triple helix formation. Such conditions are well described for peptide nucleic acids, for example in WO 95/01370 and in Wittung, P. et al. (1997) Biochemistry 36 (26): 7973–7979, to which reference is made in this respect. Because in many cases the amount of nucleic acids in the sample is not known or evident, it might be preferred to choose the amount of each probe molecule to exceed the highest expected amount of nucleic acid A in the sample. However, in order to maintain a low level of background signal, it may be advisable to choose the amount of probe molecules to be in the order of magnitude of the nucleic acid to be expected.

As described in WO 95/15971, there are several possibilities to determine the presence of any nucleic acid. In the present invention it is preferred that at least one probe molecule is labelled. Most preferred, molecule B has a label attached. Further preferred, either the nucleic acid A or the molecule(s) C has an immobilizable label or has been immobilized. The ruling principle is that within the complex containing the nucleic acid to be determined and the probe molecules, there is at least one reporter moiety and/or at least one immobilizable moiety.

An example of a specific embodiment of a method of the present invention is shown in FIG. 5. The analyte nucleic acid (long strand) is contacted with a pair of primers, one of which is labelled immobilizably, for example by having a biotin moiety at the 5'phosphate end. After amplification by PCR, the strands incorporating the biotinylated primer have been labelled immobilizably. Those strands will be used as analyte nucleic acids A in the detection according to the method of the invention. The sample is then supplied with two probe molecules C being designed such that they can bind adjacently to each other to the labelled strand by Watson-Crick basepairing. Further the sample is supplied with probe molecules B, which are shorter in length than the overall binding sequence of molecules C and are capable of Hoogsteen basepairing to form a triple stranded region as outlined above. This molecule B contains a detectable label.

The arrow on the left side of FIG. 5 indicates the case in which the amplicon produced in PCR is really the nucleic acid to be determined. Then the probe molecules B and C can form the correct triple stranded complex. This complex can be determined after immobilization on a solid support coated with streptavidin, removal of any excess probe molecules and label by washing, and thereafter detection of the presence or amount of detectable label on the solid support. The method of detection will of course depend upon the label used, e.g. in case of electrochemiluminescently labelled probes, the electrochemiluminscence will be created and detected. Any nucleic acids or amplicons not to be detected (not containing the correct double helix binding region for adjacently binding the molecules C will not be detected, as shown following the right arrow in FIG. 5. This shows that even in the unlikely event, that both probe molecules C1 and C2 can, by chance, bind to nucleic acid A, it is not detected if they are not bound exactly next to each other. In this case probe molecule B cannot participate in a thermostable complex ABC1 C2, and therefore the analyte A will not be detectably labelled and, even if immobilized to the solid phase, will not be subject to determination.

We have shown that by increasing the length of the Watson-Crick binding molecule (C), the overall stability of an intended triplex structure, ABC, can be increased. The probes B and C both contain a sequence of bases complementary to the short triple helix region (for example a homopurine tract), which functions as the target for triplex formation. Because of this, two molecules of probe B or two identical molecules of C may theoretically form competing triplex structures within the target sequence, but by use of modified bases and/or backbone and by controlling conditions of hybridization formation of the correct triplex structure ABC can be ensured.

We have also demonstrated that two adjacently bound Watson-Crick pairing oligos (C), which each covers part of the triplex region, can stabilize Hoogsteen binding sufficiently for triplex formation, including the small oligo B, to occur. Once bound, this oligo will confer additional stability to the triplex, but whether or not a particular Hoogsteen oligo is going to remain bound depends mainly on the off-rate of the Watson-Crick oligo(s). Thus, our results indicate that triplex formation is initiated by Watson-Crick binding, which is the limiting step, and that also melting is initiated by the dissociation of the Watson-Crick basepairing, which of course leads to instantaneous dissociation of the Hoogsteen bonding.

These observations have a number of implications: First, the number of bases at the site of recognition, which actually participate in bonding and stabilization of the triplex structure, are not limited to those within the triplex region itself, allowing e.g. mismatch discrimination also in adjacent positions. Second, the range within which the thermal stability of the triplex structure can be modulated is broadened, together with the panel of parameters which can be applied to control thermal stability under various assay conditions. Third, the cooperative binding of two Watson-Crick pairing probes C to two half target sites can be exploited to further enhance the feasibility of triplex structures to discriminate mismatches. Fourth, the formation of the intended triplex structure can be taken as a verification that two Watson-Crick pairing probes C have actually been bound right next to each other on the target nucleic acid strand. Finally, triplex formation involving a short, labelled, Hoogsteen binding probe will act as a double verification that the correct target sequence has been identified, since the second step of the triplex formation (Hoogsteen binding) is crucially dependent on the first step (Watson-Crick binding). In such a sceme the labelled probe will not bind to any nucleic acid except when the first probe(s) (C) has been correctly hybridized to its target sequence.

The finding that a triplex can be stabilized by increasing the length of only the Watson-Crick strand is novel and unexpected. Conditions of hybridization can be monitored to allow a short probe to bind by Hoogsteen binding, only when stabilized by a longer Watson-Crick binding probe.

The option of including a mixed sequence, adjacent to the triplex motif, in the complete target site for triplex structure formation, confers additional ways of modulating overall stability, by making triplex formation dependent on base sequences outside the actual triplex region delimited by the Hoogsteen strand.

By using cooperatively bound Watson-Crick probes (split probes) to stabilize the Hoogsteen strand, nucleobases located even further away from the triplex region itself can affect overall stability of the triplex structure. At the same time, the use of cooperatively bound Watson-Crick oligos enhances the specificity of the overall complex. This is because the discriminative power of two split Watson-Crick probes. e.g. towards single base mutations, is higher than that of a single probe of similar length, since the split probes will tolerate less degeneracy in the target region for hybridization.

The fact that the short triplex forming PNA needs stabilization by Watson-Crick binding PNA can be used to verify that two split probes are actually hybridized adjacently to each other on the target molecule, since they will not give sufficient stabilization to the triplex, if gaps are found or introduced between them.

The present invention provides the possibility to use universal probes B. Because B is relatively short, as C is selective, it can be choosen in sequence such that it can be used for determinations of different analytes, thus less probe synthesis is necessary for different assays. In addition, the same labelled oligo can be used to detect different target nucleic acids simultaneously.

The following examples describe the invention further:

EXAMPLES

General:

PNA oligos and monomers were synthesized according to WO 96/02558 and as described for automated synthesis (Koch, T. et al. (1997) J. Peptide Res. 49: 80–88) on an ABI 433 synthesizer. All DNA-oligonucleotides are single stranded and linear.

$NH_2$ designates the $CONH_2$ end of a PNA (end which was attached to the solid phase during chemical synthesis), H means the amino end of the PNA.

Example 1

Formation of a Complex from a Nucleic Acid to be Determined and Molecules B and C Given the appropiate conditions of hybridization a short PNA oligo (B) will bind to the analyte (A) via Hoogsteen basepairing only when stabilized by another, longer PNA oligo binding to the analyte (A) by Watson-Crick basepairing (depicted in FIG. 1a). Under similar conditions of hybridization the short PNA oligo (B) alone is not able to form stable triplex structures with the analyte (A) (depitched in FIG. 1b). This has been shown experimentally and the results are presented in FIG. 6.

As molecules were used:
A: DNA 12-mer: 5'-TCCAGAAGATAC-3' (SEQ.ID.NO. 1)
B: PNA 6-mer: H-TCTTCT-$NH_2$
C: PNA 12-mer: H-GTATCTTCTGGA-$NH_2$ The conditions for the triplex formation are as follows: One pmol radiolabelled DNA oligo (A) was mixed with the PNA oligos (amounts according to the table below) in a total volume of 8 μL buffer: 100 mM NaCl; 0.1 mM EDTA; 10 mM $NaH_2PO_4$, pH 5). The reaction was heat denatured for 2 min. at 95° C., and incubated for 2 hours. Products were analysed by 10% polyacrylamide gel electrophoresis, followed by autoradiography.

Numbers 1) through 9) refer to lanes in the autoradiogram shown in FIG. 6:
FIG. 6a) Lanes:
1) A(1 pmol)
2) A(1 pmol)+B(1 pmol)
3) A(1 pmol)+B(2 pmol)
4) A(1 pmol)+B(4 pmol)
5) A(1 pmol)+B(10 pmol)
6) A(1 pmol)+B(2 pmol)+C(1 pmol)
7) A(1 pmol)+B(2 pmol)+C(2 pmol)
8) A(1 pmol)+B(2 pmol)+C(4 pmol)
9) A(1 pmol)+B(2 pmol)+C(10 pmol)
FIG. 6b) Lanes:
1) A(1 pmol)
2) A(1 pmol)+C(1 pmol)
3) A(1 pmol)+C(2 pmol)
4) A(1 pmol)+C(4 pmol)
5) A(1 pmol)+C(10 pmol)
6) A(1 pmol)+C(2 pmol)+B(1 pmol)
7) A(1 pmol)+C(2 pmol)+B(2 pmol)
8) A(1 pmol)+C(2 pmol)+B(4 pmol)
9) A(1 pmol)+C(2 pmol)+B(10 pmol)

The gel shows that incubation of increasing amount of B with 1 pmol A does not result in any detectable hybrids and only the DNA oligo (A) is seen in the gel (FIG. 6a, lane 1–5). When keeping the amount of A and B constant and mixing with increasing amounts of C a triplex product is formed between A, B and C (FIG. 6a, lane 6 and 7), and after addition of surplus amounts of C an additional triplex product, between A and two molecules of C, is formed (FIG. 6a, lane 8 and 9). A fainter band can be seen in lanes 6–9 which indicates formation of small amounts of duplex between A and C. In FIG. 6b the DNA oligo alone is seen at the bottom of the gel, but after addition of increasing amounts of C both duplex and triplex formation can be seen, of which the triplex structure is the preferred product (lanes 2–5). Keeping the amount of A and C constant and adding increasing amounts of B, results in the formation of the triplex involving A, B and C whereas the triplex between A and two molecules of C is completely out-competed. These results indicate that under these conditions of hybridization the short PNA oligo (B) is not able to form stable products with A, but when present together with both A and C it will participate in the formation of an ABC triplex, outcompeting also the formation of a $AC_2$ triplex.

Example 2

Differentiation Between Nucleic Acids Having a Single Base Difference, by Formation of a Triple Helix Complex Using Two Molecules C1 and C2 as well as a Probe B This experiment is directed to a preferred mode of the invention using two split probes. The results are presented as the autoradiogram in FIG. 7. The following compounds are used in the experiment (sequences involved in triple helix formation are underlined, symmetric case):
A1: DNA 16-mer: 5'-CGTCCAGAAGATACCG-3' (nucleic acid to be determined) (SEQ.ID.NO. 2)
A2: DNA 16-mer: 5'-CGTGCAGAAGATACCG-3' (nucleic acid not to be determined) (SEQ.ID.NO. 3)
B: PNA 6-mer: H-TCTTCT-$NH_2$
C1: PNA 8-mer: H-CGGTATCT-$NH_2$
C2: PNA 8-mer: H-TCTGGACG-$NH_2$ The experimental conditions are as follows: One pmol radiolabelled DNA oligo (A1 or A2) was mixed with the PNA oligos (amounts according to the table below) in a total volume of 8 μL buffer: 100 mM NaCl, 0.1 mM EDTA; 10 mM $NaH_2PO_4$, pH 5). The reaction was heat denatured for 2 min. at 95° C., and incubated for 2 hours. Products were analysed by 10% polyacrylamide gel electrophoresis, followed by autoradiography.

Numbers 1) through 10) refer to lanes in the autoradiogram shown in FIG. 7:

FIG. 7a) Lanes:
1) A1(1 pmol)
2) A1(1 pmol)+B(2 pmol)
3) A1(1 pmol)+C1(2 pmol)
4) A1(1 pmol)+C2(2 pmol)
5) A1(1 pmol)+B(2 pmol)+C1(2 pmol)
6) A1(1 pmol)+B(2 pmol)+C2(2 pmol)
7) A1(1 pmol)+B(2 pmol)+C1/C2(1/1 pmol)
8) A1(1 pmol)+B(2 pmol)+C1/C2(2/2 pmol)
9) A1(1 pmol)+B(2 pmol)+C1/C2(4/4 pmol)
10) A1(1 pmol)+B(2 pmol)+C1/C2(10/10 pmol)

FIG. 7b) Lanes:
1) A2(1 pmol)
2) A2(1 pmol)+B(2 pmol)
3) A2(1 pmol)+C1(2 pmol)
4) A2(1 pmol)+C2(2 pmol)
5) A2(1 pmol)+B(2 pmol)+C2(2 pmol)
6) A2(1 pmol)+B(2 pmol)+C2(2 pmol)
7) A2(1 pmol)+B(2 pmol)+C1/C2(1/1 pmol)
8) A2(1 pmol)+B(2 pmol)+C1/C2(2/2 pmol)
9) A2(1 pmol)+B(2 pmol)+C1/C2(4/4 pmol)
10) A2(1 pmol)+B(2 pmol)+C1/C2(10/10 pmol)

As can be seen in FIG. 7a neither B, C1 nor C2 is able to form stable hybrids with the analyte A1 alone (lanes 2–6), and only when all components A. B, C1 and C2 are present a stable triplex structure will be formed (lanes 7–10). If a mismatch is introduced between the analyte (A2) and one of the WC-binding probes (C2) the triplex formation is strongly inhibited (FIG. 7b, lanes 7–10).

Example 3

Differentiation Between Nucleic Acids Differing by a Single Base Insertion.

In this determination there were used two split probes as in example 2. The nucleic acid to be determined differs from a nucleic acid not to be determined by a single base insertion into the latter. The probes C1 and C2 are chosen such that they will bind with a gap of one base between them to the nucleic acid not to be determined, but with only a nick in the complex when bound to the nucleic acid to be determined (sequences involved in triple helix formation underlined, asymmetric case):

The molecules used are:
A1: DNA 40-mer (nucleic acid to be determined):
    5'-GCTTGTAGTCCTGCTGAGAGAACGTGCGGGCG-ATTTGCC-3' (SEQ.ID.NO. 4)
A2: DNA 40-mer (nucleic acid not to be determined):
    5'-GCTTGTAGTCCTGCTTGAGATGAACGTGCGGG-CGAWTTGC-3' (SEQ.ID.NO. 5)
B: PNA 6-mer: H-TCTCTT-NH$_2$
C1: PNA 15-mer: H-ATCGCCCGCACGTTC-NH,
C2: PNA 15-mer: H-TCTCAAGCAGGACTA-NH$_2$ The experimental conditions are as follows: One pmol radiolabelled DNA oligo (A1 or A2) was mixed with the PNA oligos (amounts according to the table below) in a total volume of 8 μL buffer: 100 mM NaCl; 0.1 mM EDTA; 10 mM NaH$_2$PO$_4$, pH 5). The reaction was heat denatured for 2 min. at 95° C., and incubated for 2 hours. Products were analysed by 10% polyacrylamide gel electrophoresis, followed by autoradiography.

Numbers 1) through 12) refer to lanes in the autoradiogram shown in FIG. 8:

FIG. 8) Lanes:
1) A1(1 pmol)
2) A1(1 pmol)+C1(10 pmol)
3) A1(1 pmol)+C2(10 pmol)
4) A1(1 pmol)+C1/C2 (10/10 pmol)
5) A1(1 pmol)+B(10 pmol)+C1/C2(10/10 pmol)
6) A1(1 pmol)+B(10 pmol)
7) A2(1 pmol)
8) A2(1 pmol)+C1(10 pmol)
9) A2(1 pmol)+C2(10 pmol)
10) A2(1 pmol)+C 1/C2 (10/10 pmol)
11) A2(1 pmol)+B(10 pmol)+C1/C2(10/10 pmol)
12) A2(1 pmol)+B(10 pmol)

Each of the PNA probes C1 and C2 are able to form duplex with the analyte (A1 or A2) either alone (lanes 2–3,8–9) or together (lanes 4 and 10). When the two duplex forming PNA oligos C1 and C2 are bound adjacently to each other, a short triplex forming PNA oligo B is able to bind, via Hoogsteen basepairing, to form a triplex structure (lane 5). If C1 and C2 are separated by as little as one nucleobase, the triplex forming oligo B will not bind (lane 11) and only the complex between the analyte and C1/C2 is seen.

Example 4

Differentiation Using a Competitor Probe D

Figure 11:
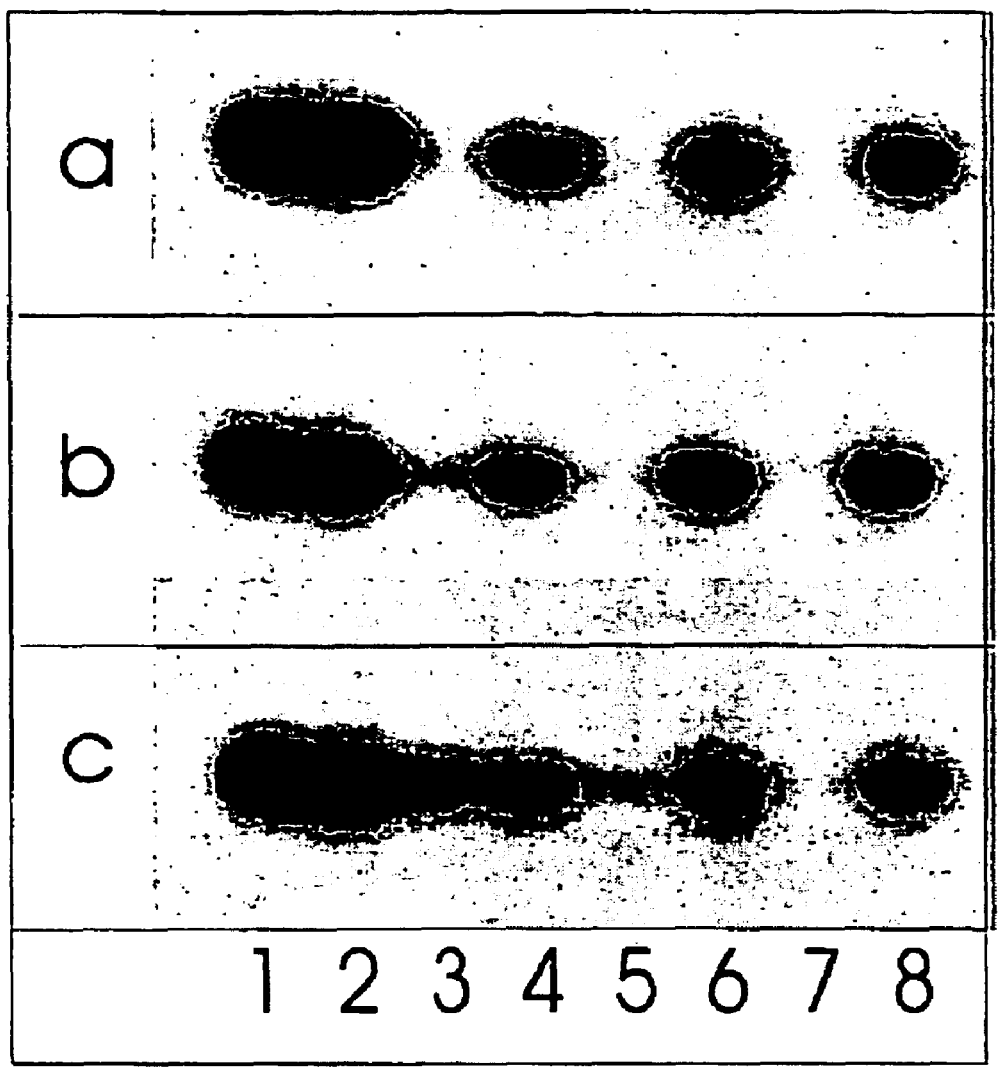
FIG. 11 shows three different combinations of PNA detection probes tested for their ability to bind their corresponding DNA oligos and for cross-hybridization to a related DNA oligo containing different single base substitutions with respect to the target DNA oligos. Hybridization was assayed either with or without increasing amounts of a competitor PNA complementary to the control oligo, but one nucleobase shorter than the detection probes.

This experiment is an example of improved specificity of detection using two molecules C1 and C2, a labelled molecule B, capable of triplex formation by Hoogsteen binding, and a molecule D, able to hybridize to the target A (depicted in FIG. 10). The results of the experiment is presented in FIG. 11. The following compounds were used:

A: DNA 22-mer: 5'-CTTGTGGTGGAAAGCTTTGCG-3' (SEQ.ID.NO. 6)
A1: DNA 22-mer: 5'-CCTGTGGTGGAAAGCTTTTGCG-3' (SEQ.ID.NO. 7)
A2: DNA 22-mer: 5'-TGTGTGGTGGAAAGCTTTGCG-3' (SEQ.ID.NO. 8)
A3: DNA 22-mer: 5'-CTTTTGGTGGAAAGCTTTTGCG-3' (SEQ.ID.NO. 9)
B: PNA 6-mer: Kemptide-JJTTTJ-gly-NH$_2$, (J denotes pseudoisocytosine)
C1: PNA 11-mer: H-CGCAAAAGCTT-NH$_2$
C2-1: PNA 11-mer: H-TCCACCACAGG-NH$_2$
C2-2: PNA II-mer: H-TCCACCACACA-NH,
C2-3: PNA 11-mer: H-TCCACCAAAAG-NH$_2$
D: PNA 10-mer: H-CCACCACAAG-NH$_2$ The PNA B was radiolabelled via the kemptide-motif (Koch,T. et al., Tetrahedron Lett. (1995) 36: 6933–36) and 1 pmol was mixed with 1 pmol target (A, A1, A2 or A3) and various amounts of PNA probes C and D, in a total volume of 10 μL buffer: 100 mM NaCl; 0.1 mM EDTA; 10 mM NaH$_2$PO$_4$, pH 5.0). The mixture was heat denatured at 95° C. for 2 min. before hybridizing at 10 min. at RT. Two μ L loading buffer was added and half of the reaction (lanes 1 and 2) or one third of the reaction (lanes 3–8) was run on 5% polyacrylamide gelelectrophoresis and visualized by autoradiography.

Three different combinations of PNA detection probes (FIGS. 11a, b, and c) were tested for their ability to bind their corresponding target DNA oligo (A1, A2 and A3, respectively) and for crosshybridization to a related control DNA oligo (A) containing different single base-substitutions with respect to the target DNA oligos. Hybridization was assayed either without or with increasing ammount of a competitor PNA (D) complementary to the control oligo A, but one nucleobase shorter than the detection probes (C2-1, C2-2 and C2-3). The probe C1, covering the other half of the DNA target region, was common to all targets and, thus, used in all assays.

The reactions, corresponding to the lanes 1–8 on FIG. 11a were:

| 1) | A (1 pmol) | C1 (10 pmol) | C2-1 (10 pmol) | B (1 pmol) |            |
|----|------------|--------------|----------------|------------|------------|
| 2) | A1 (1 pmol)| C1 (10 pmol) | C2-1 (10 pmol) | B (1 pmol) |            |
| 3) | A (1 pmol) | C1 (10 pmol) | C2-1 (10 pmol) | B (1 pmol) | D (10 pmol)|
| 4) | A1 (1 pmol)| C1 (10 pmol) | C2-1 (10 pmol) | B (1 pmol) | D (10 pmol)|
| 5) | A (1 pmol) | C1 (10 pmol) | C2-1 (10 pmol) | B (1 pmol) | D (15 pmol)|
| 6) | A1 (1 pmol)| C1 (10 pmol) | C2-1 (10 pmol) | B (1 pmol) | D (15 pmol)|
| 7) | A (1 pmol) | C1 (10 pmol) | C2-1 (10 pmol) | B (1 pmol) | D (20 pmol)|
| 8) | A1 (1 pmol)| C1 (10 pmol) | C2-1 (10 pmol) | B (1 pmol) | D (20 pmol)|

The reactions, corresponding to the lanes 1–8 on FIG. 11b were:

| 1) | A (1 pmol) | C1 (10 pmol) | C2-2 (10 pmol) | B (1 pmol) |            |
|----|------------|--------------|----------------|------------|------------|
| 2) | A2 (1 pmol)| C1 (10 pmol) | C2-2 (10 pmol) | B (1 pmol) |            |
| 3) | A (1 pmol) | C1 (10 pmol) | C2-2 (10 pmol) | B (1 pmol) | D (10 pmol)|
| 4) | A2 (1 pmol)| C1 (10 pmol) | C2-2 (10 pmol) | B (1 pmol) | D (10 pmol)|
| 5) | A (1 pmol) | C1 (10 pmol) | C2-2 (10 pmol) | B (1 pmol) | D (15 pmol)|
| 6) | A2 (1 pmol)| C1 (10 pmol) | C2-2 (10 pmol) | B (1 pmol) | D (15 pmol)|
| 7) | A (1 pmol) | C1 (10 pmol) | C2-2 (10 pmol) | B (1 pmol) | D (20 pmol)|
| 8) | A2 (1 pmol)| C1 (10 pmol) | C2-2 (10 pmol) | B (1 pmol) | D (20 pmol)|

The reactions, corresponding to the lanes 1–8 on FIG. 11c were:

| 1) | A (1 pmol) | C1 (10 pmol) | C2-3 (10 pmol) | B (1 pmol) |            |
|----|------------|--------------|----------------|------------|------------|
| 2) | A3 (1 pmol)| C1 (10 pmol) | C2-3 (10 pmol) | B (1 pmol) |            |
| 3) | A (1 pmol) | C1 (10 pmol) | C2-3 (10 pmol) | B (1 pmol) | D (10 pmol)|
| 4) | A3 (1 pmol)| C1 (10 pmol) | C2-3 (10 pmol) | B (1 pmol) | D (10 pmol)|
| 5) | A (1 pmol) | C1 (10 pmol) | C2-3 (10 pmol) | B (1 pmol) | D (15 pmol)|
| 6) | A3 (1 pmol)| C1 (10 pmol) | C2-3 (10 pmol) | B (1 pmol) | D (15 pmol)|
| 7) | A (1 pmol) | C1 (10 pmol) | C2-3 (10 pmol) | B (1 pmol) | D (20 pmol)|
| 8) | A3 (1 pmol)| C1 (10 pmol) | C2-3 (10 pmol) | B (1 pmol) | D (20 pmol)|

In the absense of PNA competitor molecule D, the combination of PNA probe molecules C1, C2 and, B is able to bind and form a triplex structure, both with the control target, having a single mismatch (lane 1), and with the fully complementary target (lane 2). The inclusion of 10 pmol competitor (lane 3) still gives rise to some cross-hybridization with one set of detection probes (FIG. 11c) but all cross-hybridization to the control target could be prevented by adding higher amount of PNA competitor D to the reactions (lanes 5, 7, and 8). With the complementary targets triplex formation is still seen even in the presence of competitor (lanes 4, 6 and 8).

What is claimed is:

1. A method for determining the presence or amount of a nucleic acid A, comprising: (a) forming a triple stranded complex between said nucleic acid A, a nucleic acid A binding probe B, said nucleic acid A binding probe B having a base sequence and a binding region which binds to nucleic acid A, and one or more nucleic acid A binding probes C, wherein said one or more nucleic acid A binding probes C, in the aggregate, comprise a base sequence different from the base sequence of nucleic acid A binding probe B and an aggregate binding region wherein said aggregate binding region, which binds to nucleic acid A, is longer as compared with the binding region of probe B; and (b) determining the presence or amount of said triple stranded complex as an indication of the presence or amount of nucleic acid A, and wherein said triple stranded complex comprises two different nucleic acid A binding probes C which bind to different regions of nucleic acid A in the triple stranded region.

2. The method according to claim 1, wherein said nucleic acid A binding probe B comprises a binding region of 4 to 10 bases.

3. The method according to claim 1 wherein said two different nucleic acid A binding probes C of the triple stranded complex form an aggregate binding region which is comprised of two distinct triple helical binding regions, wherein each distinct triple helical binding region is formed from the binding of the two different probes C each to a distinct, non-overlapping, region on nucleic acid A.

4. The method according to claim 3 wherein said two different nucleic acid A binding probes C bind juxtaposed on nucleic acid A.

5. The method according to claim 3 wherein said triple stranded complex is at least six bases in length and each of the two different nucleic acid A binding probes C individually contribute at least one but less than eleven bases to said triple stranded complex.

6. The method according to claim 1, wherein said binding region of nucleic acid A binding probe B comprises only pyrimidine bases but the aggregate binding region of the one or more nucleic acid A binding probes C comprises at least one non-pyrimidine base.

7. The method according to claim 1, wherein at least one of said nucleic acid A binding probes has been chemically modified to destabilize triple helix formation occurring by either of: (a) two nucleic acid A binding probes B binding to one nucleic acid A; or (b) two of said nucleic acid A binding probes C binding with one nucleic acid A.

8. The method according to claim 1, wherein a first nucleic acid not to be determined is differentiated from said nucleic acid A by a difference in the base sequence located within the binding region of the nucleic acid A binding probe B.

9. The method according to claim 1, wherein at least one of said nucleic acid A binding probes is a nucleic acid analogue.

10. The method according to claim 9 wherein said nucleic acid analogue is a peptide nucleic acid.

11. The method according to claim 1, wherein at least one of said nucleic acid A binding probes is a polymer of the general Formula I

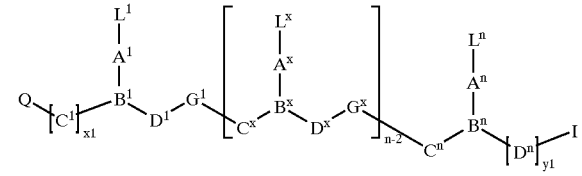

Formula I wherein n is an integer of from at least 3;

x is an integer of from 2 to n−1;

each of $L^1$–$L^n$ is a ligand independently selected from the group consisting of hydrogen, hydroxy, ($C_1$–$C_4$) alkanoyl, naturally occurring nucleobases, non-naturally occurring nucleobases, aromatic moieties, DNA intercalators, nucleobase-binding groups, heterocyclic moieties, reporter ligands and chelating moieties, wherein at least one of $L^1$–$L^n$, preferably at least one of $L^2$–$L^{n-1}$ is a non-nucleobase electron acceptor or a donor moiety and at least 2 of $L^1$–$L^n$ being a nucleobase binding group, or a naturally or non-naturally occurring nucleobase;

each of $C^1$–$C^n$ is $(CR^6R^7)_y$ (preferably $CR^6R^7$, $CHR^6CHR^7$ or $CR^6R^7CH_2$) where $R^6$ is hydrogen and $R^7$ is selected from the group consisting of the side chains of naturally occurring alpha amino acids, or $R^6$ and $R^7$ are independently selected from the group consisting of hydrogen, ($C_1$–$C_6$)alkyl, aryl, aralkyl, heteroaryl, hydroxy, ($C_1$–$C_6$)alkoxy, ($C_1$–$C_6$)alkylthio, $NR^3R^4$ and $SR^5$, where $R^3$ and $R^4$ are as defined below, and $R^5$ is hydrogen, ($C_1$–$C_6$)alkyl, hydroxy, ($C_1$–$C_6$) alkoxy, or ($C_1$–$C_6$)alkylthio-substituted ($C_1$–$C_6$)alkyl or $R^6$ and $R^7$ taken together complete an alicyclic or heterocyclic system; or $C^1$–$C^n$ is CO, CS, $CNR^3$;

each of $D^1$–$D^n$ is $(CR^6R^7)_z$ (preferably $CR^6R^7$, $CHR^6CHR^7$ or $CH_2CR^6R^7$) where $R^6$ and $R^7$ are as defined above;

each of y and z is zero or an integer from 1 to 10, the sum y+z being at least 2, preferably greater than 2, but not more than 10;

each of $G^1$–$G^{n-1}$ is —$NR^3CO$—, —$NR^3CS$—, —$NR^3SO$— or —$NR^3SO^{2-}$—, in either orientation, where $R^3$ is as defined below;

each of $A^1$–$A^n$ and $B^1$–$B^n$ are selected such that:

(a) $A^1$–$A^n$ is a group of formula (I/A), (I/B), (I/C) or (I/D), and $B^1$–$B^n$ is N or $R^3N+$; or (b) $A^1$–$A^n$ is a group of formula (I/D) and $B^1$–$B^n$ is CH;

Formula I/A

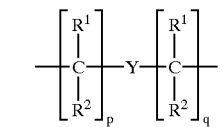

Formula I/B

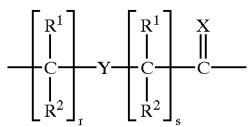

Formula I/C

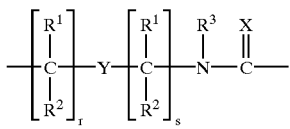

Formula I/D

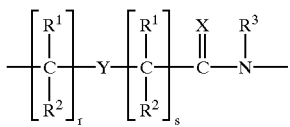

wherein:

X is O, S, Se, $NR^3$, $CH_2$ or $C(CH_3)_2$;

Y is a single bond, O, S or $NR^4$;

each of p and q is zero or an integer from 1 to 5, (the sum p+q being preferably not more than 5);

each of r and s is zero or an integer from 1 to 5, (the sum r+s being preferably not more than 5);

each $R^1$ and $R^2$ is independently selected from the group consisting of hydrogen, $(C_1$–$C_4)$alkyl which may be hydroxy- or $(C_1$–$C_4)$alkoxy- or $(C_1$–$C_4)$alkylthio-substituted, hydroxy, $(C_1$–$C_4)$alkoxy, $(C_1$–$C_4)$alkylthio, amino and halogen; and each $R^3$ and $R^4$ is independently selected from the group consisting of hydrogen, $(C_1$–$C_4)$alkyl, hydroxy- or alkoxy- or alkylthio-substituted $(C_1$–$C_4)$alkyl, hydroxy, $(C_1$–$C_6)$-alkoxy, $(C_1$–$C_6)$-alkylthio and amino;

Q and I is independently selected from —$CO_2H$, —$CONR'R''$, —$SO_3H$ or —$SO_2NR'R''$ or an activated derivative of —$CO_2H$ or —$SO_3H$ and —$NR'R'''$ where R', R" and R''' are independently selected from the group consisting of hydrogen, alkyl, amino protecting groups, reporter ligands, intercalators, chelators, peptides, proteins, carbohydrates, lipids, steroids, nucleosides, nucleotides, nucleotide diphosphates, nucleotide triphosphates, oligonucleotides, including both oligoribonucleotides and oligodeoxyribonucleotides, oligonucleosides and soluble and non-soluble polymers and as well as nucleic acid binding moieties and each of x1 and y1 is an integer of from 0 to 10.

12. A method according to claim 1, wherein at least one of said nucleic acid A binding probes is a polymer of the general Formula I Formula I

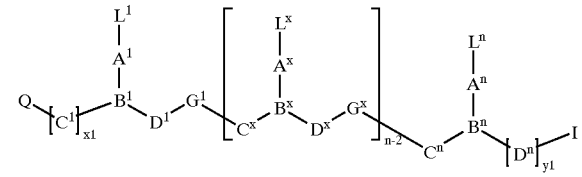

wherein n is an integer of from at least 3, x is an integer of from 2 to n−1, each of $L^1$–$L^n$ is a ligand independently selected from the group consisting of hydrogen, hydroxy, $(C_1$–$C_4)$ alkanoyl, naturally occurring nucleobases, non-naturally occurring nucleobases, aromatic moieties, DNA intercalators, nucleobase-binding groups, heterocyclic moieties, reporter ligands and chelating moieties, wherein at least one of $L^1$–$L^n$, preferably at least one of $L^2$–$L^{n-1}$ is a non-nucleobase electron acceptor or a donor moiety and at least 2 of $L^1$–$L^n$ being a nucleobase binding group, or a naturally or non-naturally occurring nucleobase;

each of $C^1$–$C^n$ is $(CR^6R^7)_y$ (preferably $CR^6R^7$, $CHR^6CHR^7$ or $CR^6R^7CH_2$) where $R^6$ is hydrogen and $R^7$ is selected from the group consisting of the side chains of naturally occurring alpha amino acids, or $R^6$ and $R^7$ are independently selected from the group consisting of hydrogen, $(C_1$–$C_6)$alkyl, aryl, aralkyl, heteroaryl, hydroxy, $(C_1$–$C_5)$alkoxy, $(C_1$–$C_6)$alkylthio, $NR^3R^4$ and $SR^5$, where $R^3$ and $R^4$ are as defined below, and $R^5$ is hydrogen, $(C_1$–$C_6)$alkyl, hydroxy, $(C_1$–$C_6)$ alkoxy, or $(C_1$–$C_6)$alkylthio-substituted $(C_1$–$C_6)$alkyl or $R^6$ and $R^7$ taken together complete an alicyclic or heterocyclic system; or $C_1$–$C^n$ is CO, CS, $CNR^3$;

each of $D^1$–$D^n$ is $(CR^6R^7)_z$ (preferably $CR^6R^7$, $CHR^6CHR^7$ or $CH_2CR^6R^7$) where $R^6$ and $R^7$ are as defined above;

each of y and z is zero or an integer from 1 to 10, the sum y+z being at least 2, preferably greater than 2, but not more than 10;

each of $G^1$–$G^{n-1}$ is —$NR^3CO$—, —$NR^3CS$—, —$NR^3SO$— or —$NR^3SO^{2-}$—, in either orientation, where $R^3$ is as defined below;

each of $A^1$–$A^n$ and $B^1$–$B^n$ are selected from (Ia), (Ib) or (Ic) such that:

(Ia): $B^1$–$B^n$ is N and $A^1$–$A^n$ is —CO—$(CH_2)_6$—

(Ib): $B^1$–$B^n$ is N and $A^1$–$A^n$ is —CO—$NR^3$—$(CH_2)_2$—

(Ic): $B^1$–$B^n$ is CH and $A^1$–$A^n$ is —$NR^3$—CO—$(CH_2)_2$—

Q and I is independently selected from —$CO_2H$, —$CONR'R''$, —$SO_3H$ or —$SO_2NR'R''$ or an activated derivative of —$CO_2H$ or —$SO_3H$ and —$NR'R''$ where R', R" and R''' are independently selected from the group consisting of hydrogen, alkyl, amino protecting groups, reporter ligands, intercalators, chelators, peptides, proteins, carbohydrates, lipids, steroids, nucleosides, nucleotides, nucleotide diphosphates, nucleotide triphosphates, oligonucleotides, including both oligoribonucleotides and oligodeoxyribonucleotides, oligonucleosides and soluble and non-soluble polymers and as well as nucleic acid binding moieties and each of x1 and y1 is an integer of from 0 to 10.

13. The method according to claim 1, wherein at least one of said nucleic acid A binding probes comprise at least one monomer subunit of general Formula III

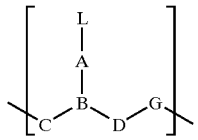

Formula III each of L is a ligand independently selected from the group consisting of hydrogen, hydroxy, $(C_1-C_4)$ alkanoyl, naturally occurring nucleobases, non-naturally occurring nucleobases, aromatic moieties, DNA intercalators, nucleobase-binding groups, heterocyclic moieties, reporter ligands and chelating moieties, wherein at least one of L is a non-nucleobase electron acceptor or a donor moiety and at least 2 of L being a nucleobase binding group, or a naturally or non-naturally occurring nucleobase;

each of C is $(CR^6R^7$ where $R^6$ is hydrogen and $R^7$ is selected from the group consisting of the side chains of naturally occurring alpha amino acids, or $R^6$ and $R^7$ are independently selected from the group consisting of hydrogen, $(C_1-C_6)$alkyl, aryl, aralkyl, heteroaryl, hydroxy, $(C_1-C_6)$alkoxy, $(C_1-C_6)$alkylthio, $NR^3R^4$ and $SR^5$, where $R^3$ and $R^4$ are as defined below, and $R^5$ is hydrogen, $(C_1-C_6)$alkyl, hydroxy, $(C_1-C_6)$alkoxy, or $(C_1-C_6)$alkylthio-substituted $(C_1-C_6)$alkyl or $R^6$ and $R^7$ taken together complete an alicyclic or heterocyclic system; or C is CO, CS, $CNR^3$;

each of D is $(CR^6R^7)$ where $R^6$ and $R^7$ are as defined above;

each of y and z is zero or an integer from 1 to 10, the sum y+z being at least 2;

each of G is —$NR^3CO$—, —$NR^3CS$—, —$NR^3SO$— or —$NR^3SO^{2-}$, in either orientation, where $R^3$ is as defined below;

each of A and B are selected such that:
(a) A is a group of formula (I/A), (I/B), (I/C) or (I/D), and B is N or $R^3N+$; or
(b) A is a group of formula (I/D) and B is CH;

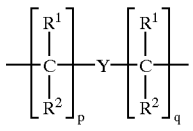

Formula I/A

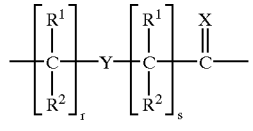

Formula I/B

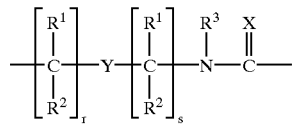

Formula I/C

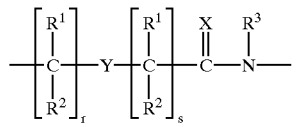

Formula I/D wherein:
X is O, S, Se, $NR^3$, $CH_2$ or $C(CH_3)_2$; Y is a single bond, O, S or $NR^4$;
each of p and q is zero or an integer from 1 to 5,
each of r and s is zero or an integer from 1 to 5,
each $R^1$ and $R^2$ is independently selected from the group consisting of hydrogen, $(C_1-C_4)$alkyl which may be hydroxy- or $(C_1-C_4)$alkoxy- or $(C_1-C_4)$alkylthio-substituted, hydroxy, $(C_1-C_4)$alkoxy, $(C_1-C_4)$alkylthio, amino and halogen; and
each $R^3$ and $R^4$ is independently selected from the group consisting of hydrogen, $(C_1-C_4)$alkyl, hydroxy- or alkoxy- or alkylthio-substituted $(C_1-C_4)$alkyl, hydroxy, $(C_1-C_6)$-alkoxy, $(C_1-C_6)$-alkylthio and amino;
where R', R" and R'" are independently selected from the group consisting of hydrogen, alkyl, amino protecting groups, reporter ligands, intercalators, chelators, peptides, proteins, carbohydrates, lipids, steroids, nucleosides, nucleotides, nucleotide diphosphates, nucleotide triphosphates, oligonucleotides, including both oligoribonucleotides and oligodeoxyribonucleotides, oligonucleosides and soluble and non-soluble polymers and as well as nucleic acid binding moieties and each of x1 and y1 is an integer of from 0 to 10.

14. The method according to claim 1, wherein said triple stranded complex is more thermostable than a triple stranded complex formed by two nucleic acid A binding probes B binding with one nucleic acid A.

15. The method according to claim 1, wherein said triple stranded complex is more thermostable than a triple stranded complex formed from either of: (a) two nucleic acid A binding probes B binding with one nucleic acid A; or (b) two of said nucleic acid A binding probes C binding with one nucleic acid A.

16. The method according to claim 1, wherein said binding region of nucleic acid A binding probe B has an asymmetric base sequence.

17. The method according to claim 1, wherein said binding region of nucleic acid A binding probe B has a symmetric base sequence.

18. The method according to claim 1, wherein said aggregate binding region of the one or more nucleic acid A binding probes C has a length of at least 6 bases.

19. The method according to claim 1, wherein said nucleic acid A binding probe B is bound to nucleic acid A via Hoogsteen base pairing and the one or more nucleic acid A binding probes C are bound to nucleic acid A via Watson Crick base pairing.

20. The method according to claim 1, wherein at least one of said nucleic acid A binding probes is labeled and the presence of said label In the triple stranded complex is used for determining the presence or amount of the nucleic acid A.

21. A method for determining the presence or amount of a nucleic acid A, comprising: (a) forming a triple stranded complex between said nucleic acid A, a nucleic acid A binding probe B, said nucleic acid A binding probe B having a base sequence and a binding region which binds to nucleic acid A, and one or more nucleic acid A binding probes C, wherein said one or more nucleic acid A binding probes C, in the aggregate, comprise a base sequence different from the base sequence of nucleic acid A binding probe B and an aggregate binding region wherein said aggregate binding region, which binds to nucleic acid A, is longer as compared with the binding region of Probe B; and (b) determining the presence or amount of said triple stranded complex as an indication of the presence or amount of nucleic acid A, and wherein a first nucleic acid not to be determined is differentiated from said nucleic acid A by a difference in the base sequence located outside the binding region of the nucleic acid A binding probe B but within the aggregate binding region of the one or more nucleic acid A binding probes C.

22. A method for determining the presence or amount of a nucleic acid A, comprising: (a) forming a triple stranded complex between said nucleic acid A, a nucleic acid A binding probe B, said nucleic acid A binding probe B having a base sequence and a binding region which binds to nucleic acid A, and one or more nucleic acid A binding probes C, wherein said one or more nucleic acid A binding probes C, in the aggregate, comprise a base sequence different from the base sequence of nucleic acid A binding probe B and an aggregate binding region wherein said aggregate binding region, which binds to nucleic acid A, is longer as compared with the binding region of probe B; and (b) determining the presence or amount of said triple stranded complex as an indication of the presence or amount of nucleic acid A, and wherein a reaction mixture is used for forming the triple stranded complex, said reaction mixture containing a competitive probe D which can compete with at least one nucleic acid A binding probe C in binding to nucleic acid A, but which is incapable of participating in the formation of the triple stranded complex.

23. A triple stranded complex comprising a nucleic acid A, a nucleic acid A binding probe B, said nucleic acid A binding probe B having a base sequence and a binding region which binds to nucleic acid A, and one or more nucleic acid A binding probes C wherein said one or more nucleic acid A binding probes C, in the aggregate, comprise a base sequence different from the sequence of nucleic acid A binding probe B and an aggregate binding region wherein said aggregate binding region, which binds to nucleic acid A, is longer as compared with the binding region of nucleic acid A binding probe B, and wherein said triple stranded complex comprises two different nucleic acid A binding C probes.

24. The complex according to claim 23, wherein said nucleic acid A binding probe B comprises a binding region of 4 to 10 bases.

25. The complex according to claim 23 wherein said two different nucleic acid A binding probes C of the triple stranded complex form an aggregate binding region which is comprised of two distinct triple helical binding regions, wherein each distinct triple helical binding region is formed from the binding of the two different nucleic acid A binding probes C each to a distinct, non-overlapping, region on nucleic acid A.

26. The complex according to claim 25 wherein said two different nucleic acid A binding probes C bind juxtaposed on nucleic acid A.

27. The complex according to claim 23, wherein said binding region of nucleic acid A binding probe B comprises only pyrimidine bases but the aggregate binding region of the one or more nucleic acid A binding probes C comprises at least one non-pyrimidine base.

28. The complex according to claim 23, wherein at least one of said nucleic acid A binding probes is a nucleic acid analogue.

29. The complex according to claim 23, wherein said nucleic acid analogue is a peptide nucleic acid.

30. The complex according to claim 23, wherein said triple stranded complex is more thermostable than a triple stranded complex formed by two nucleic acid A binding probes B binding with one nucleic acid A.

31. The complex according to claim 23, wherein said triple stranded complex is more thermostable than a triple stranded complex formed from either of: (a) two nucleic acid A binding probes B binding with one nucleic acid A; or (b) two of said nucleic acid A binding probes C binding with one nucleic acid A.

32. The complex according to claim 23, wherein said aggregate binding region of the one or more nucleic acid A binding probes C has a length of at least 6 bases.

33. The complex according to claim 23, wherein said nucleic acid A binding probe B is bound to nucleic acid A via Hoogsteen base pairing and the one or more nucleic acid A binding probes C are bound to nucleic acid A via Watson Crick base pairing.

34. The complex according to claim 23, wherein at least one of said nucleic acid A binding probes is labelled and the presence of said label in the triple stranded complex is used for determining the presence or amount of the nucleic acid A.

35. A method of forming a triple stranded binding complex comprising reacting a nucleic acid molecule A with a nucleic acid A binding probe B, said nucleic acid A binding probe B having a base sequence and binding region which binds to nucleic acid A, and one or more nucleic acid A binding probes C, wherein said one or more nucleic acid A binding probes C, in the aggregate, comprise a base sequence different from the sequence of nucleic acid A binding probe B and an aggregate binding region wherein said aggregate binding region, which binds to nucleic acid A, is longer as compared with the binding region of nucleic acid A binding probe B, and wherein said triple stranded complex comprises two different nucleic acid A binding probes C.

36. The method according to claim 35, wherein said nucleic acid A binding probe B comprises a binding region of 4 to 10 bases.

37. The method according to claim 35, wherein said binding region of nucleic acid A binding probe B comprises only pyrimidine bases but the aggregate binding region of the one or more nucleic acid A binding probes C comprises at least one non-pyrimidine base.

38. The method according to claim 35, wherein said nucleic acid A binding probe B is bound to nucleic acid A via Hoogsteen base pairing and the one or more nucleic acid A binding probes C are bound to nucleic acid A via Watson Crick base pairing.

39. The method according to claim 35, wherein at least one of said nucleic acid A binding probes is a nucleic acid analogue.

40. The method according to claim 35, wherein said nucleic acid analogue is a peptide nucleic acid.

41. The method according to claim 35, wherein said triple stranded complex is more thermostable than a triple stranded complex formed by two nucleic acid A binding probes B binding with one nucleic acid A.

42. The method according to claim 35, wherein said triple stranded complex is more thermostable than a triple stranded complex formed from either of: (a) two nucleic acid A binding probes B binding with one nucleic acid A; or (b) two of said nucleic acid A binding probes C binding with one nucleic acid A.

43. The method according to claim 35, wherein said aggregate binding region of the one or more nucleic acid A binding probes C has a length of at least 6 bases.

44. A method of forming a triple stranded binding complex comprising reacting a nucleic acid molecule A with a nucleic acid A binding probe B, said nucleic acid A binding probe B having a base sequence and binding region which binds to nucleic acid A, and one or more nucleic acid A binding probes C, wherein said one or more nucleic acid A binding probes C, in the aggregate, comprise a base sequence different from the sequence of nucleic acid A binding probe B and an aggregate binding region wherein said aggregate binding region, which binds to nucleic acid A, is longer as compared with the binding region of nucleic acid A binding probe B, wherein two different nucleic acid A binding probes C of the triple stranded complex form an aggregate binding region which is comprised of two distinct triple helical binding regions, and wherein each distinct triple helical binding region is formed from the binding of the two different nucleic acid A binding probes C each to a distinct, non-overlapping, region on nucleic acid A.

45. The method according to claim 44 wherein said two different nucleic acid A binding probes C bind juxtaposed on nucleic acid A.

46. A method for determining the presence or amount of a nucleic acid A, comprising: (a) forming a triple stranded complex between said nucleic acid A, a nucleic acid A binding probe B, said nucleic acid A binding probe B having a base sequence and a binding region which binds to nucleic acid A, and two nucleic acid A binding probes C, wherein said two nucleic acid A binding probes C, in the aggregate, comprise a base sequence different from the base sequence of nucleic acid A binding probe B and an aggregate binding region wherein said aggregate binding region, which binds to nucleic acid A, is longer as compared with the binding region of nucleic acid A binding probe B; and (b) determining the presence or amount of said nucleic acid A by measuring for the presence or amount of said triple stranded complex.

47. The method according to claim 46 wherein said two nucleic acid A binding probes C of the triple stranded complex are different and form an aggregate binding region which is comprised of two distinct triple helical binding regions, wherein each distinct triple helical binding region is formed from the binding of the two different nucleic acid A binding probes C each to a distinct, non-overlapping, region on nucleic acid A.

48. The method according to claim 47 wherein said two different nucleic acid A binding probes C bind juxtaposed on nucleic acid A.

49. The method according to claim 47 wherein said triple stranded complex is at least six bases in length and each of the two different nucleic acid A binding probes C individually contribute at least one but less than eleven bases to said triple stranded complex.

* * * * *

SEQUENCE LISTING

<160> NUMBER OF SEQ ID NOS: 9

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tccagaagat ac                                                          12

<210> SEQ ID NO 2
<211> LENGTH: 16
<212> TYPE: DNA

-continued

```
<213> ORGANISM: Artificial Sequence
<220> FEATURE:
<223> OTHER INFORMATION: Description of Artificial Sequence: Synthetic
      oligonucleotide

<400> SEQUENCE: 2
cgtccagaag ataccg                                                     16

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cgtgcagaag ataccg                                                     16

<210> SEQ ID NO 4
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gcttgtagtc ctgcttgaga gaacgtgcgg gcgatttgcc                           40

<210> SEQ ID NO 5
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gcttgtagtc ctgcttgaga tgaacgtgcg ggcgatttgc                           40

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cttgtggtgg aaagcttttg cg                                              22

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
cctgtggtgg aaagcttttg cg                                              22

<210> SEQ ID NO 8
<211> LENGTH: 22
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 8
tgtgtggtgg aaagcttttg cg                                            22

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
cttttggtgg aaagcttttg cg                                            22
```